US010327645B2

(12) United States Patent
Rourke et al.

(10) Patent No.: US 10,327,645 B2
(45) Date of Patent: Jun. 25, 2019

(54) IMAGING TECHNIQUES USING AN IMAGING GUIDEWIRE

(71) Applicant: Vascular Imaging Corporation, Rancho Cordova, CA (US)

(72) Inventors: Howard Neil Rourke, Sacramento, CA (US); Michael J. Eberle, Fair Oaks, CA (US); Diana Margaret Tasker, Sacramento, CA (US)

(73) Assignee: Vascular Imaging Corporation, Rancho Cordova, CA (US)

( * ) Notice: Subject to any disclaimer, the term of this patent is extended or adjusted under 35 U.S.C. 154(b) by 368 days.

(21) Appl. No.: 15/026,521

(22) PCT Filed: Oct. 1, 2014

(86) PCT No.: PCT/US2014/058643
§ 371 (c)(1),
(2) Date: Mar. 31, 2016

(87) PCT Pub. No.: WO2015/051003
PCT Pub. Date: Apr. 9, 2015

(65) Prior Publication Data
US 2016/0242653 A1    Aug. 25, 2016

Related U.S. Application Data

(60) Provisional application No. 61/886,965, filed on Oct. 4, 2013.

(51) Int. Cl.
*A61B 5/05* (2006.01)
*A61B 5/00* (2006.01)
(Continued)

(52) U.S. Cl.
CPC .......... *A61B 5/0095* (2013.01); *A61B 1/0017* (2013.01); *A61B 5/0084* (2013.01);
(Continued)

(58) Field of Classification Search
None
See application file for complete search history.

(56) References Cited

U.S. PATENT DOCUMENTS 3,789,841 A   2/1974  Antoshkiw
3,906,938 A   9/1975  Fleischhacker
(Continued)

FOREIGN PATENT DOCUMENTS

EP          1238264 B1    12/2004
WO     WO-2002019903 A1    3/2002
(Continued)

OTHER PUBLICATIONS

"European Application Serial No. 13779472.3, Office Action dated Aug. 2, 2017", 5 pgs.
(Continued)

*Primary Examiner* — Jonathan Cwern
(74) *Attorney, Agent, or Firm* — Schwegman Lundberg & Woessner, P.A.

(57) ABSTRACT

Techniques for imaging are disclosed. In one example, the disclosure is directed to a sensor positioned on an elongate optical fiber. The sensor comprises a plurality of blazed Bragg gratings configured to generate acoustic energy for imaging a region in response to a first optical signal, an interferometer configured to sense acoustic energy from the region and to provide a responsive second optical signal, the interferometer including a first fiber Bragg grating (FBG) and a second FBG, wherein the plurality of blazed Bragg gratings are positioned between the first and second FBGs.

9 Claims, 7 Drawing Sheets

(51) Int. Cl.
*G01H 9/00* (2006.01)
*G02B 6/293* (2006.01)
*A61B 1/00* (2006.01)
*A61B 90/30* (2016.01)

(52) U.S. Cl.
CPC .......... *A61B 5/0097* (2013.01); *A61B 5/6851* (2013.01); *A61B 5/7203* (2013.01); *A61B 5/742* (2013.01); *G01H 9/004* (2013.01); *G02B 6/29319* (2013.01); *A61B 2090/306* (2016.02); *A61B 2576/00* (2013.01)

(56) References Cited

U.S. PATENT DOCUMENTS

| | | |
|---|---|---|
| 3,995,623 A | 12/1976 | Blake et al. |
| 4,554,929 A | 11/1985 | Samson et al. |
| 4,712,566 A | 12/1987 | Hok |
| 4,907,332 A | 3/1990 | Christian et al. |
| 4,917,097 A | 4/1990 | Proudian et al. |
| 4,917,102 A | 4/1990 | Miller et al. |
| 4,932,959 A | 6/1990 | Horzewski et al. |
| 4,936,310 A | 6/1990 | Engstrom et al. |
| 4,941,473 A | 7/1990 | Tenerz et al. |
| 4,955,384 A | 9/1990 | Taylor et al. |
| 4,958,642 A | 9/1990 | Christian et al. |
| 4,961,433 A | 10/1990 | Christian |
| 4,966,163 A | 10/1990 | Kraus et al. |
| 4,967,753 A | 11/1990 | Haase et al. |
| 5,007,434 A | 4/1991 | Doyle et al. |
| 5,018,529 A | 5/1991 | Tenerz |
| 5,050,606 A | 9/1991 | Tremulis |
| 5,059,851 A | 10/1991 | Corl et al. |
| 5,085,223 A | 2/1992 | Lars et al. |
| 5,125,058 A | 6/1992 | Tenerz et al. |
| 5,125,137 A | 6/1992 | Corl et al. |
| 5,135,503 A | 8/1992 | Abrams |
| 5,163,445 A | 11/1992 | Christian et al. |
| 5,167,233 A | 12/1992 | Eberle et al. |
| 5,195,375 A | 3/1993 | Tenerz |
| 5,226,421 A | 7/1993 | Frisbie et al. |
| 5,226,423 A | 7/1993 | Tenerz et al. |
| 5,240,437 A | 8/1993 | Christian |
| 5,246,007 A | 9/1993 | Frisbie et al. |
| 5,271,404 A | 12/1993 | Corl et al. |
| 5,325,860 A | 7/1994 | Seward et al. |
| 5,341,818 A | 8/1994 | Abrams et al. |
| 5,348,481 A | 9/1994 | Ortiz |
| 5,358,409 A | 10/1994 | Obara |
| 5,411,476 A | 5/1995 | Abrams et al. |
| 5,413,508 A | 5/1995 | Obara |
| 5,423,331 A | 6/1995 | Wysham |
| 5,427,118 A | 6/1995 | Nita et al. |
| 5,514,128 A | 5/1996 | Hillsman et al. |
| 5,517,989 A | 5/1996 | Frisbie et al. |
| 5,520,194 A | 5/1996 | Miyata et al. |
| 5,551,301 A | 9/1996 | Cowan |
| 5,558,101 A | 9/1996 | Brooks et al. |
| 5,571,094 A | 11/1996 | Sirhan |
| 5,581,144 A | 12/1996 | Corl et al. |
| 5,668,320 A | 1/1997 | Cowan |
| 5,603,327 A | 2/1997 | Eberle et al. |
| 5,637,089 A | 6/1997 | Abrams et al. |
| RE35,648 E | 11/1997 | Tenerz et al. |
| 5,688,234 A | 11/1997 | Frisbie |
| 5,694,946 A | 12/1997 | Tenerz et al. |
| 5,695,111 A | 12/1997 | Nanis et al. |
| 5,715,827 A | 2/1998 | Corl et al. |
| 5,740,596 A | 4/1998 | Corl et al. |
| 5,797,856 A | 8/1998 | Frisbie et al. |
| 5,873,835 A | 2/1999 | Hastings et al. |
| 5,897,819 A | 4/1999 | Miyata et al. |
| 5,908,385 A | 6/1999 | Chechelski et al. |
| 5,910,364 A | 6/1999 | Miyata et al. |
| 5,938,624 A | 8/1999 | Akerfeldt et al. |
| 5,984,853 A | 11/1999 | Smith |
| 6,025,670 A | 2/2000 | Corl et al. |
| 6,049,958 A | 4/2000 | Eberle et al. |
| 6,089,103 A | 7/2000 | Smith |
| 6,090,052 A | 7/2000 | Akerfeldt et al. |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,165,292 A | 12/2000 | Abrams et al. |
| 6,167,763 B1 | 1/2001 | Tenerz et al. |
| 6,175,669 B1 | 1/2001 | Colston et al. |
| 6,182,513 B1 | 2/2001 | Stemme et al. |
| 6,191,862 B1 | 2/2001 | Swanson et al. |
| 6,196,980 B1 | 3/2001 | Akerfeldt et al. |
| 6,198,557 B1 * | 3/2001 | Dultz ............ H04L 27/28 398/102 |
| 6,210,339 B1 | 4/2001 | Kiepen et al. |
| 6,241,651 B1 | 6/2001 | Smith et al. |
| 6,248,083 B1 | 6/2001 | Smith et al. |
| 6,265,792 B1 | 7/2001 | Granchukoff |
| 6,280,539 B1 | 8/2001 | Abrams et al. |
| 6,312,380 B1 | 11/2001 | Hoek et al. |
| 6,336,906 B1 | 1/2002 | Hammarstrom et al. |
| 6,337,737 B1 | 1/2002 | Chang et al. |
| 6,343,514 B1 | 2/2002 | Smith |
| 6,379,369 B1 | 4/2002 | Abrams et al. |
| 6,390,993 B1 | 5/2002 | Cornish et al. |
| 6,409,677 B1 | 6/2002 | Tulkki |
| 6,419,745 B1 | 7/2002 | Burkett et al. |
| 6,423,012 B1 | 7/2002 | Kato et al. |
| 6,428,336 B1 | 8/2002 | Akerfeldt |
| 6,445,939 B1 | 9/2002 | Swanson et al. |
| 6,459,486 B1 * | 10/2002 | Udd ............ G01H 9/004 356/478 |
| 6,461,301 B2 | 10/2002 | Smith |
| 6,461,453 B1 | 10/2002 | Abrams et al. |
| 6,491,648 B1 | 12/2002 | Cornish et al. |
| 6,517,481 B2 | 2/2003 | Hoek et al. |
| 6,546,804 B2 | 4/2003 | Stemme et al. |
| 6,552,796 B2 | 4/2003 | Magnin et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,592,570 B2 | 7/2003 | Abrams et al. |
| 6,602,228 B2 | 8/2003 | Nanis et al. |
| 6,615,067 B2 | 9/2003 | Hoek et al. |
| 6,615,667 B2 | 9/2003 | Smith |
| 6,659,957 B1 | 12/2003 | Vardi et al. |
| 6,666,829 B2 | 12/2003 | Cornish et al. |
| 6,672,172 B2 | 1/2004 | Tulkki et al. |
| 6,673,025 B1 | 1/2004 | Richardson et al. |
| 6,682,608 B2 | 1/2004 | Abrams et al. |
| 6,692,446 B2 | 2/2004 | Hoek |
| 6,695,915 B2 | 2/2004 | Burkett et al. |
| 6,733,819 B2 | 5/2004 | Burkett et al. |
| 6,754,608 B2 | 6/2004 | Svanerudh et al. |
| 6,767,327 B1 | 7/2004 | Corl et al. |
| 6,779,257 B2 | 8/2004 | Kiepen et al. |
| 6,852,109 B2 | 2/2005 | Winston |
| 6,884,225 B2 | 4/2005 | Kato et al. |
| 6,891,984 B2 | 5/2005 | Petersen et al. |
| 6,908,442 B2 | 6/2005 | von Malmborg et al. |
| 6,926,674 B2 | 8/2005 | Tenerz et al. |
| 6,938,474 B2 | 9/2005 | Melvås |
| 6,976,965 B2 | 12/2005 | Corl et al. |
| 6,993,974 B2 | 2/2006 | Tenerz et al. |
| 7,003,184 B2 | 2/2006 | Ronnekleiv et al. |
| 7,011,636 B2 | 3/2006 | Tenerz |
| 7,021,152 B2 | 4/2006 | Tenerz |
| 7,097,620 B2 | 8/2006 | Corl et al. |
| 7,117,703 B2 | 10/2006 | Kato et al. |
| 7,150,723 B2 | 12/2006 | Meguro et al. |
| H2180 H | 2/2007 | Brininstool |
| 7,182,757 B2 | 2/2007 | Miyata et al. |
| 7,187,453 B2 | 3/2007 | Belleville |
| 7,222,539 B2 | 5/2007 | Tulkki |
| 7,241,286 B2 | 7/2007 | Atlas |
| 7,244,319 B2 | 7/2007 | Abrams et al. |

(56) References Cited

U.S. PATENT DOCUMENTS

| | | | |
|---|---|---|---|
| 7,245,789 B2 * | 7/2007 | Bates | A61B 5/0097 359/285 |
| 7,254,946 B1 | 8/2007 | Quinn | |
| 7,259,862 B2 | 8/2007 | Duplain | |
| 7,263,894 B2 | 9/2007 | Tenerz | |
| 7,274,956 B2 | 9/2007 | Mott et al. | |
| RE39,863 E | 10/2007 | Smith | |
| 7,326,088 B2 | 2/2008 | Tulkki | |
| 7,331,236 B2 | 2/2008 | Smith et al. | |
| 7,343,811 B2 | 3/2008 | Tenerz et al. | |
| 7,399,283 B2 | 7/2008 | Kato | |
| 7,447,388 B2 | 11/2008 | Bates et al. | |
| 7,450,989 B2 | 11/2008 | Svanerudh | |
| 7,472,601 B1 | 1/2009 | Tenerz et al. | |
| 7,527,594 B2 | 5/2009 | Vardi et al. | |
| 7,532,920 B1 | 5/2009 | Ainsworth et al. | |
| 7,553,444 B2 | 6/2009 | Kato | |
| 7,645,233 B2 | 1/2010 | Tulkki et al. | |
| 7,660,492 B2 | 2/2010 | Bates et al. | |
| 7,676,910 B2 | 3/2010 | Kiepen et al. | |
| 7,680,363 B2 | 3/2010 | Wakahara et al. | |
| 7,689,071 B2 | 3/2010 | Belleville et al. | |
| 7,724,148 B2 | 5/2010 | Samuelsson et al. | |
| 7,753,852 B2 | 7/2010 | Maschke | |
| 7,762,954 B2 | 7/2010 | Nix et al. | |
| 7,775,988 B2 | 8/2010 | Pijls | |
| 7,775,992 B2 | 8/2010 | von Malmborg et al. | |
| 7,914,458 B2 | 3/2011 | Hossack et al. | |
| 7,918,947 B2 | 4/2011 | Kato | |
| 7,931,603 B2 | 4/2011 | Von Malmborg et al. | |
| 7,946,997 B2 | 5/2011 | Hubinette | |
| 7,967,761 B2 | 6/2011 | Smith | |
| 7,967,762 B2 | 6/2011 | Corl et al. | |
| 7,998,089 B2 | 8/2011 | Smith | |
| 8,038,628 B2 | 10/2011 | von Malmborg et al. | |
| 8,059,923 B2 | 11/2011 | Bates et al. | |
| 8,298,156 B2 | 10/2012 | Manstrom et al. | |
| 8,317,715 B2 | 11/2012 | Belleville et al. | |
| 8,412,312 B2 | 4/2013 | Judell et al. | |
| 8,478,384 B2 | 7/2013 | Schmitt et al. | |
| 8,485,985 B2 | 7/2013 | Manstrom | |
| 8,583,218 B2 | 11/2013 | Eberle | |
| 8,641,639 B2 | 2/2014 | Manstrom et al. | |
| 8,676,299 B2 | 3/2014 | Schmitt et al. | |
| 8,677,299 B1 | 3/2014 | Alpert et al. | |
| 9,936,881 B2 | 4/2018 | Rourke et al. | |
| 2002/0041735 A1 | 4/2002 | Cai et al. | |
| 2002/0059827 A1 | 5/2002 | Smith | |
| 2003/0175034 A1 | 9/2003 | Noe | |
| 2003/0185509 A1 * | 10/2003 | Bailey | G02B 6/0218 385/37 |
| 2003/0220588 A1 | 11/2003 | Tenerz et al. | |
| 2004/0067000 A1 | 4/2004 | Bates et al. | |
| 2004/0180581 A1 | 9/2004 | von Malmborg et al. | |
| 2004/0225232 A1 | 11/2004 | Malmborg et al. | |
| 2005/0121734 A1 | 6/2005 | Degertekin et al. | |
| 2005/0200855 A1 | 9/2005 | Mcinnes et al. | |
| 2005/0200941 A1 | 9/2005 | Yao | |
| 2005/0232531 A1 | 10/2005 | Hadley et al. | |
| 2006/0183992 A1 | 8/2006 | Kawashima | |
| 2006/0241483 A1 | 10/2006 | Nix et al. | |
| 2006/0241503 A1 | 10/2006 | Schmitt et al. | |
| 2006/0241505 A1 | 10/2006 | Ahmed et al. | |
| 2007/0078500 A1 | 4/2007 | Ryan et al. | |
| 2007/0156019 A1 | 7/2007 | Larkin et al. | |
| 2007/0255144 A1 | 11/2007 | Tulkki et al. | |
| 2008/0119739 A1 | 5/2008 | Vardi et al. | |
| 2008/0161696 A1 | 7/2008 | Schmitt et al. | |
| 2008/0165366 A1 | 7/2008 | Schmitt | |
| 2009/0036754 A1 | 2/2009 | Pons et al. | |
| 2009/0180730 A1 | 7/2009 | Foster et al. | |
| 2010/0016717 A1 * | 1/2010 | Dogra | A61B 5/0059 600/437 |
| 2010/0087732 A1 | 4/2010 | Eberle et al. | |
| 2010/0199773 A1 | 8/2010 | Zhou | |
| 2010/0228112 A1 | 9/2010 | Von Malmborg | |
| 2010/0234698 A1 | 9/2010 | Manstrom et al. | |
| 2010/0241008 A1 | 9/2010 | Belleville et al. | |
| 2011/0071405 A1 | 3/2011 | Judell et al. | |
| 2011/0144502 A1 | 6/2011 | Zhou et al. | |
| 2012/0108943 A1 | 5/2012 | Bates et al. | |
| 2012/0136244 A1 | 5/2012 | Manstrom | |
| 2012/0220883 A1 | 8/2012 | Manstrom et al. | |
| 2012/0227505 A1 | 9/2012 | Belleville | |
| 2012/0238869 A1 | 9/2012 | Schmitt et al. | |
| 2012/0310081 A1 | 12/2012 | Adler et al. | |
| 2013/0051731 A1 | 2/2013 | Belleville | |
| 2013/0096409 A1 | 4/2013 | Hiltner et al. | |
| 2013/0131523 A1 | 5/2013 | Suchecki et al. | |
| 2013/0215919 A1 * | 8/2013 | Aflatouni | H01S 5/06817 372/38.01 |
| 2013/0218032 A1 | 8/2013 | Belleville | |
| 2013/0303914 A1 | 11/2013 | Hiltner et al. | |
| 2013/0310698 A1 | 11/2013 | Judell et al. | |
| 2013/0317359 A1 | 11/2013 | Wilson et al. | |
| 2013/0317372 A1 | 11/2013 | Eberle et al. | |
| 2013/0324864 A1 | 12/2013 | Manstrom | |
| 2013/0331714 A1 | 12/2013 | Manstrom et al. | |
| 2014/0005558 A1 | 1/2014 | Gregorich | |
| 2014/0024950 A1 | 1/2014 | Hiltner et al. | |
| 2014/0039325 A1 | 2/2014 | Belleville | |
| 2014/0058275 A1 | 2/2014 | Gregorich et al. | |
| 2014/0081244 A1 | 3/2014 | Voeller et al. | |
| 2014/0094697 A1 | 4/2014 | Petroff et al. | |
| 2014/0100462 A1 | 4/2014 | Rourke et al. | |
| 2014/0107624 A1 | 4/2014 | Belleville | |
| 2014/0180031 A1 | 6/2014 | Anderson | |
| 2014/0180034 A1 | 6/2014 | Hoseit et al. | |
| 2014/0200438 A1 | 7/2014 | Millett et al. | |
| 2015/0141843 A1 | 5/2015 | Eberle et al. | |
| 2015/0141854 A1 | 5/2015 | Eberle et al. | |
| 2016/0018593 A1 | 1/2016 | Tasker et al. | |

FOREIGN PATENT DOCUMENTS

| | | |
|---|---|---|
| WO | WO-2007041542 A2 | 4/2007 |
| WO | WO-2012061935 A1 | 5/2012 |
| WO | WO-2013177577 A2 | 11/2013 |
| WO | WO-2013177577 A3 | 11/2013 |
| WO | WO-2014055729 A1 | 4/2014 |
| WO | WO-2015051003 A1 | 4/2015 |

OTHER PUBLICATIONS

"U.S. Appl. No. 13/902,334, Response filed Jun. 12, 2017 to Restriction Requirement dated Jan. 19, 2017", 11 pgs.

"U.S. Appl. No. 13/902,334, Restriction Requirement dated Jan. 19, 2017", 7 pgs.

"U.S. Appl. No. 14/045,189, Non Final Office Action dated Feb. 7, 2017", 17 pgs.

"U.S. Appl. No. 14/045,189, Response filed Jul. 26, 2017 to Non Final Office Action dated Feb. 7, 2017", 14 pgs.

"U.S. Appl. No. 14/045,189, Response filed Jul. 6, 2016 to Final Office Action dated Feb. 16, 2016", 16 pgs.

"U.S. Appl. No. 14/045,189, Supplemental Response filed Jul. 27, 2016 to Final Office Action dated Feb. 16, 2016", 13 pgs.

"European Application Serial No. 13779472.3, Office Action dated May 10, 2016", 7 pgs.

"European Application Serial No. 13779472.3, Respose filed Sep. 19, 2016 to Office Action dated May 10, 2016", 17 pgs.

"International Application Serial No. PCT/US2014/058643, International Preliminary Report on Patentability dated Apr. 14, 2016", 8 pgs.

U.S. Appl. No. 13/902,334, Amendment filed Nov. 4, 2013, 9 pgs.

U.S. Appl. No. 14/045,189, Final Office Action dated Feb. 16, 2016, 16 pgs.

U.S. Appl. No. 14/045,189, Non Final Office Action dated Jul. 8, 2015, 12 pgs.

U.S. Appl. No. 14/045,189, Response filed Nov. 2, 2015 to Office Action dated Jul. 8, 2015, 15 pgs.

(56) References Cited

OTHER PUBLICATIONS

European Applcation Serial No. 13727763.8, Office Action dated Jan. 14, 2015, 2 pgs.
European Application Serial No. 13779472.3, Office Action dated May 18, 2015, 2 pgs.
European Application Serial No. 13779472.3, Response filed Nov. 16, 2015 to Office Action dated May 18, 2015, 14 pgs.
"Fiber optic miniature pressure sensor", .25 & .40mm Specifications, (Feb. 27, 2012), 2 pgs.
"IFU, GW, Hi-Torque Guide Wires, Global, CE", Abbott Vascular, (Feb. 8, 2010), 1-6.
International Application Serial No. PCT/US2013/042769, International Preliminary Report on Patentability dated Dec. 4, 2014, 12 pgs.
International Application Serial No. PCT/US2013/042769, International Search Report dated Mar. 10, 2014, 6 pgs.
International Application Serial No. PCT/US2013/042769, Invitation to Pay Additional Fees and Partial Search Report dated Dec. 5, 2013, 7 pgs.
International Application Serial No. PCT/US2013/042769, Written Opinion dated Mar. 10, 2014, 10 pgs.
International Application Serial No. PCT/US2013/063212, International Preliminary Report on Patentability dated Apr. 16, 2015, 9 pgs.
International Application Serial No. PCT/US2013/063212, International Search Report dated Jan. 16, 2014, 5 pgs.
International Application Serial No. PCT/US2013/063212, Written Opinion dated Jan. 16, 2014, 7 pgs.
International Application Serial No. PCT/US2014/058643, International Search Report dated Jan. 19, 2015, 3 pgs.
International Application Serial No. PCT/US2014/058643, Written Opinion dated Jan. 19, 2015, 6 pgs.
Japanese Application Serial No. 2015-514239, Voluntary Amendment filed Feb. 24, 2015, (w/ English Translation of Claims), 6 pgs.
"OPP-M Fiber optic miniature physiological* pressure sensor", [online]. [retrieved on Feb. 27, 2012]. Retrieved from the Internet: <http://opsens.com/en/industries/products/pressure/opp-m/>, (2012), 1 pg.
"Opsens Signs First Major Agreement in the Medical Field Granting Distribution Rights of its FFR Products for Japan, Korea and Taiwan in US$5 Million Transaction", Press Release, Quebec City, Quebec, (Nov. 19, 2012), 3 pgs.
"Optical Pressure & Temperature Sensing", Opsens, (Feb. 27, 2012), 29 pgs.
"Route / PROWATERflex and Rinato / PROWATER Guidewire Specifications", [online] [retrieved on Feb. 24, 2012]. Retrieved from the Internet: <http://www.asahi-intecc.com/medical/international/product/ptca_gw.php>, (2012), 1 pg.
"Scrambling to Reduce Polarization Related Impairments, Application Note", General Photonics Corporation, (Apr. 2003), 4 pgs.
Haga, Yoichi, et al., "Multi-functional Active Catheter", Sensors Update, 8(1), (Nov. 2000), 147-186.
Mineta, T, et al., "Batch fabricated flat meandering shape memory alloy actuator for active catheter", Sensors and Actuators A 88, (2001), 112-120.
Mineta, Takashi, "An active guide wire with shape memory alloy bending actuator fabricated by room temperature process", Sensors and Actuators A 97-98, (2002), 632-637.
Siebes, M., et al., "Single-Wire Pressure and Flow Velocity Measurement to Quantify Coronary Stenosis Hemodynamics and Effects of Percutaneous Interventions", Circulation, 109, (2004), 756-762.
"U.S. Appl. No. 13/902,334, Non Final Office Action dated Nov. 22, 2017", 18 pgs.
"U.S. Appl. No. 14/045,189, Notice of Allowance dated Dec. 4, 2017", 9 pgs.
"U.S. Appl. No. 13/902,334, Response filed May 2, 2018 to Non Final Office Action dated Nov. 22, 2017", 13 pgs.
"European Application Serial No. 13779472.3, Response filed Feb. 2, 2018 to Office Action dated Aug. 2, 2017", 3 pgs.
"U.S. Appl. No. 13/902,334, Final Office Action dated Jul. 19, 2018", 18 pgs.
"U.S. Appl. No. 13/902,334, Pre-Appeal Brief Request filed Nov. 5, 2018", 4 pgs.
"European Application Serial No. 13779472.3, Communication Pursuant to Article 94(3) EPC dated Jul. 4, 2018", 5 pgs.
"U.S. Appl. No. 13/902,334, Decision on Pre-Appeal Brief Request dated Jan. 25, 2019", 4 pgs.
"U.S. Appl. No. 13/902,334, Examiner Interview Summary dated Jan. 25, 2019", 2 pgs.
"U.S. Appl. No. 13/902,334, Response filed Jan. 30, 2019 to Final Office Action dated Jul. 19, 2018", 13 pgs.

* cited by examiner

IMAGING TECHNIQUES USING AN IMAGING GUIDEWIRE

This application is a U.S. National Stage Filing under 35 U.S.C. 371 from International Application No. PCT/US2014/058643, filed on Oct. 1, 2014, and published as WO 2015/051003 A1 on Apr. 9, 2015, which claims the benefit of priority under 35 U.S.C. § 119(e) of U.S. Provisional Patent Application No. 61/886,965, titled "IMAGING TECHNIQUES USING AN IMAGING GUIDEWIRE," by Rourke et al., and filed on Oct. 4, 2013, the entire content of each of which is incorporated by reference herein in its entirety.

TECHNICAL FIELD

This document pertains generally to medical devices and, in particular, to imaging guidewires.

BACKGROUND

U.S. Pat. No. 7,245,789 to Bates et al. (hereafter "Bates"), titled "Systems and Methods for Minimally-Invasive Optical-Acoustic Imaging," which issued on Jul. 17, 2007, discusses a device well suited to the unique and demanding application of cardio-vascular Imaging and also potential applications within the field of neuro-vascular imaging, among others. Bates describes a device that may include a combination of a resonant cavity within an optical fiber that acts as an ultrasound receiver, and a method for creating an ultrasound wave within the cavity for the ultrasound generator or transmit function. These functions are realized by the use of Fiber Bragg Gratings (FBGs).

The imaging guidewire in Bates may have a diameter similar to that of standard guidewires. As such, the imaging guidewire in Bates may be compatible with many existing therapies. The small diameter of the imaging guidewire in Bates may mean that it can remain in place while therapies are administered, and that it can be used to provide feedback without the need for "Catheter Exchange." Catheter exchange may be necessary for other imaging devices as the existing imaging catheters may be too large to be deployed along with a therapy. Catheter exchange may lead to an undesirable situation in which the clinician needs to exchange or swap imaging and therapy catheters several times during a procedure before the therapy has been judged as being successful. As such, catheter exchange may be time consuming and, in some cases, traumatic for the patient. With the Bates design, it is possible to both administer a therapy and have the imaging guidewire in place simultaneously, which can drastically reduce the time for a procedure and lead to a much better application of the therapy and patient outcomes by real-time monitoring.

The Bates device may image a cross-sectional slice of a vessel inside which it is inserted. The image may be referred to as a two-dimensional ("2D") image because at any given time it is imaging a single slice of the vessel. The image thickness of the single slice may be on the order of several hundred microns (0.000001 meter) to one millimeter ("mm") with a resolution that is on the order of tens of microns.

In some example implementations, existing imaging devices may generate a "pseudo" three-dimensional ("3D") image of the vessel. The pseudo-3D image may be generated over a length of the vessel that may range from a few millimeters to a few centimeters ("cm") using a technique known as "pull back." "Pull back" involves slowly retracting the imaging device along the section of the vessel to be imaged, and then using an imaging system to construct a 3D image from the individual slices captured during the pull back.

The "pull back" technique may not be ideal as it may take several minutes to complete and it is often unreliable as the imaging device is moving during the process. This can lead to smearing of the image because of vessel movement, spiral motion of the imaging device, and other effects. A smeared image may lead to loss of important detail and an inaccurate representation of the vessel.

One example technique described in Bates is to scale the imaging to 3D by replicating the sensors multiple times along a desired length of the guidewire. A technique such as Wavelength Division Multiplexing (WDM) may be used to uniquely distinguish each of the slices. In this case, a complete and unique set of optical components and electronics for each of the slices may be necessary. In one example implementation, ten slices of a vessel may require 320 receive lasers, based on 32 imaging elements on the guidewire per slice, and 10 pulsed lasers to implement the transmit function.

Overview

In general, this disclosure describes imaging techniques. The imaging techniques may provide real-time 2D or 3D imaging of a vessel. Using various techniques of this disclosure, an imaging guidewire can include multiple, independent, ultrasound transmit sections within a Fabry-Perot interferometric sensor. Each of the sections within the optical cavity may be addressed using a pulsed fiber transmit laser, e.g., using blazed FBGs. Blazed FBGs within the optical cavity may be tuned to different wavelengths. Tuning the wavelength of the transmit laser to a specific wavelength may cause the laser to resonate and interact with a specific transmit section, e.g., blazed FBG. A 3D image of the vessel may be generated by acquiring a first slice of the vessel associated with a first transmit section, changing the wavelength of the transmit laser to resonate with a second transmit section, acquiring a second slice associated with the second transmit section, and so forth, for a number of slices, e.g., ten. Then the acquired slices can be combined to form a 3D image of the vessel.

In one example, the disclosure is directed to a sensor positioned on an elongate optical fiber. The sensor comprises a plurality of blazed Bragg gratings configured to generate acoustic energy for imaging a region in response to a first optical signal, an interferometer configured to sense acoustic energy from the region and to provide a responsive second optical signal, the interferometer including a first fiber Bragg grating (FBG) and a second FBG, wherein the plurality of blazed Bragg gratings are positioned between the first and second FBGs.

In another example, the disclosure is directed to an imaging guidewire comprises an elongate guidewire core, including proximal and distal portions and a substantially cylindrical circumference, an elongate optical fiber located along a length of the guidewire core, the elongate optical fiber including a sensor positioned at the distal portion. The sensor includes a plurality of blazed Bragg gratings configured to generate acoustic energy for imaging a region in response to a first optical signal, an interferometer configured to sense acoustic energy from the region and to provide a responsive second optical signal, the interferometer including a first fiber Bragg grating (FBG) and a second FBG, wherein the plurality of blazed Bragg gratings are positioned between the first and second FBGs.

In another example, the disclosure is directed to a method comprising tuning a transmit laser to a first wavelength and, for a plurality of optical fibers, transmitting first optical signals along the plurality of optical fibers toward first blazed Bragg gratings configured to generate acoustic energies for imaging first regions in response to the first optical signals. The method further comprises sensing acoustic energies from the first regions and providing responsive second optical signals. The method further comprises tuning the transmit laser to a second wavelength and, for the plurality of optical fibers, transmitting third optical signals along the plurality of optical fibers toward second blazed Bragg gratings configured to generate acoustic energies for imaging second regions in response to the third optical signals. The method further comprises sensing acoustic energies from the second regions and providing responsive fourth optical signals. The method further comprises acquiring information from the responsive second and fourth optical signals. The method further comprises generating an image of the first and second regions from the acquired information.

In another example, the disclosure is directed to a method comprising tuning a transmit laser to a first wavelength and transmitting a first optical signal along an optical fiber toward a first blazed Bragg grating configured to generate acoustic energy for imaging a first region in response to the first optical signal. The method further comprises sensing, using an interferometer including a first fiber Bragg grating (FBG) and a second FBG, acoustic energy from the region and providing a responsive second optical signal. The method further comprises tuning the transmit laser to a second wavelength and transmitting a third optical signal along the optical fiber toward a second blazed Bragg grating configured to generate acoustic energy for imaging a second region in response to the third optical signal, wherein the first and second blazed Bragg gratings are positioned between the first and second FBGs. The method further comprises sensing, using the interferometer, acoustic energy from the second region and providing a responsive fourth optical signal. The method further comprises acquiring information from the responsive second and fourth optical signals. The method further comprises generating an image of the first and second regions from the acquired information.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In the following detailed description of examples of the invention, reference is made to the accompanying drawings which form a part hereof, and which is shown by way of illustration only, specific examples in which the invention may be practiced. It is to be understood that other examples may be utilized and structural changes may be made without departing from the scope of the present invention.

Acousto-optic sensors and imaging guidewires are well known and, as such, will not be described in detail in this disclosure. Information regarding acousto-optic sensors and imaging guidewires may be found, for example, in U.S. Pat. No. 7,245,789 to Bates et al. (hereafter "Bates"), titled "Systems and Methods for Minimally-Invasive Optical-Acoustic Imaging," the entire contents of which being incorporated herein by reference.

Figure 1A:
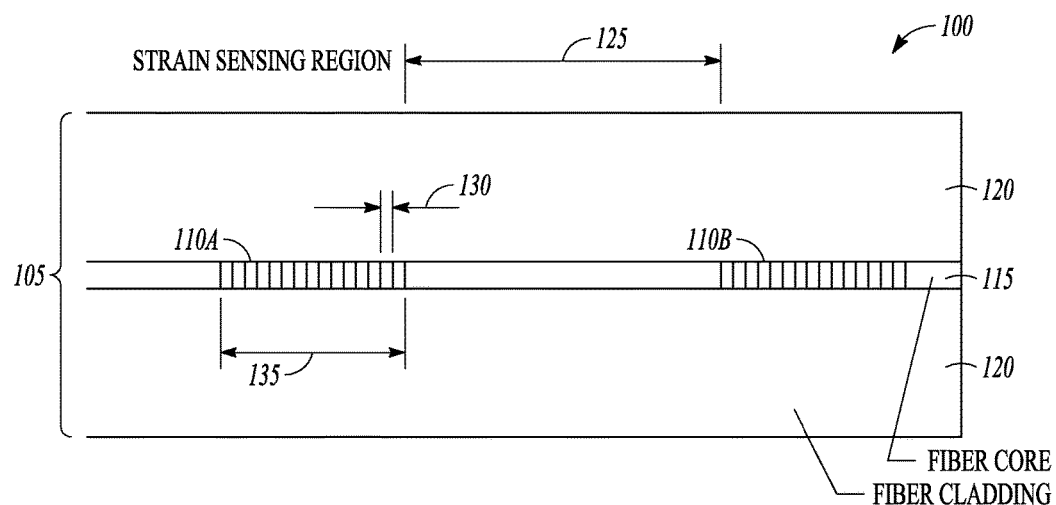
FIG. 1A illustrates generally an example that can include a portion of an optical fiber transducer, such as sized and shaped for delivery to an intravascular location.

FIG. 1A illustrates generally an example that can include a portion of an optical fiber transducer 100, such as sized and shaped for delivery to an intravascular location. The optical fiber transducer 100 can include an optical fiber assembly 105, such as including an optical fiber core 115 and a cladding 120. The optical fiber transducer 100 can include an interferometer structure, such as comprising one or more Fiber Bragg Gratings (FBGs), e.g., a Fabry-Perot interferometer. An FBG can be configured to reflect a specified proportion of incident optical energy for a specified range of wavelengths, similarly to a mirror.

A first FBG 110A can be located along the optical fiber core. The first FBG 110A can include a specified or periodic variation in the index of refraction along a longitudinal axis of the optical fiber core 115. For example, the optical fiber core 115 can have a first index of refraction, and the first FBG 110A can include portions having a second index of refraction "written" or otherwise impressed in the optical fiber core 115 in a periodic configuration, such as having a spacing between the portions having the second index that can be referred to as the period 130 of the first FBG 110A.

The first and second indices of refraction, and the period 130 of the first FBG 110A, can be used to control a range of wavelengths for which the first FBG 110A is reflective. The first and second indices of refraction and an axial length 135 of the first FBG 110A can be used to control a proportion of incident optical energy that is reflected versus transmitted through the first FBG 110A. A second FBG 110B can be located along the fiber core 115, such as separated from the first FBG 110A by a sensing region 125. A combination of the first and second FBGs 110A and 110B can establish an interferometer structure (e.g., a Fabry-Perot cavity).

Figure 1B:
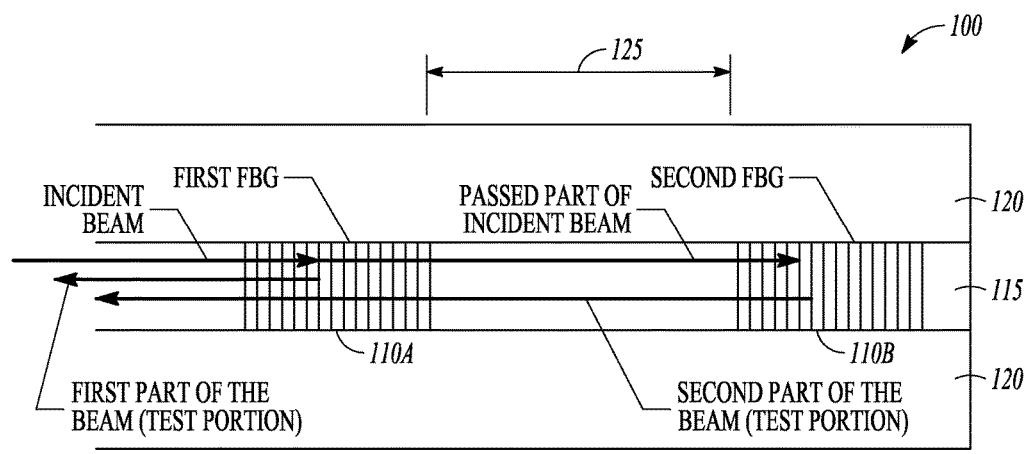
FIG. 1B illustrates generally an example that can include a portion of an optical fiber transducer, such as sized and shaped for delivery to an intravascular location.

As shown in FIG. 1B, incident optical energy (e.g., an incident beam) can be coupled to the interferometer structure established by the first and second FBGs 110A and 110B. Such optical energy can be generated by a first optical source, such as a laser (not depicted in FIG. 1B). Along the length of the optic fiber transducer, the first FBG 110A can be located more proximally to the first optical source than the second FBG 110B.

A portion of the incident optical energy can be reflected by the first FBG 110A (e.g., a "first part of the beam") and from the second FBG 110B (e.g., a "second part of the beam"). A phase relationship between the reflected portions of the optical energy can be adjusted such as by any change affecting the optical path length between the first and second FBGs 110A and 110B, such as an optical path including the sensing region 125. Such a change in optical path length can occur when one or more vibration, pressure, or strain is imparted on the optical fiber core 115 such as via the cladding 120, causing a change in the index of refraction of the optical fiber core 115 in the sensing region 125 or a physical lengthening or shortening the optical path in the sensing region 125. Such variation in the optical path length in the sensing region 125 can modulate or adjust an intensity of optical energy reflected from the interferometer structure. In this manner, the optical fiber transducer 100 can be configured to provide an acousto-optical transducer.

Figure 2:
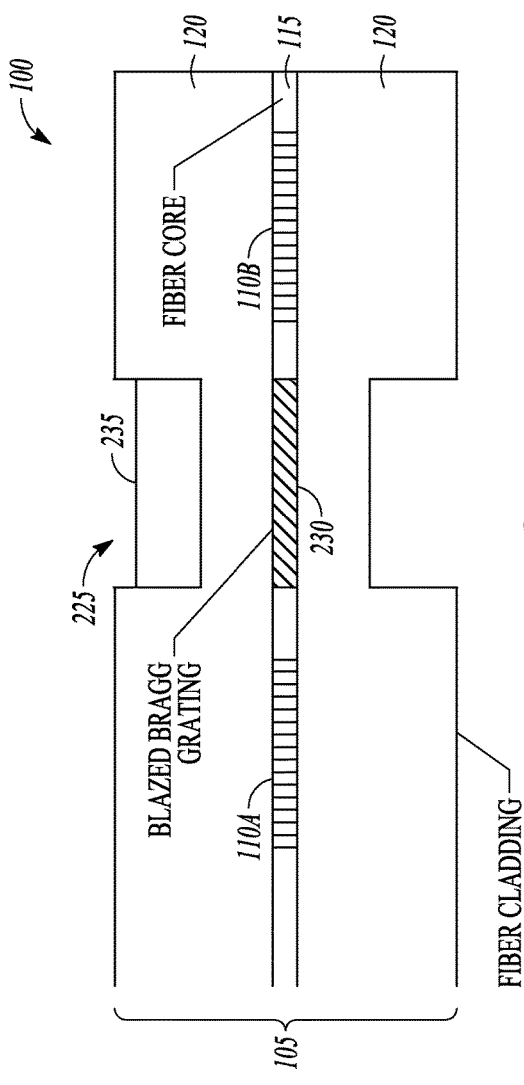
FIG. 2 is a cross-sectional schematic diagram illustrating generally one example of a distal portion of an imaging guidewire that combines an acousto-optic fiber Bragg grating ("FBG") sensor with a photoacoustic transducer.

FIG. 2 is a cross-sectional schematic diagram illustrating generally one example of a distal portion of an imaging guidewire that combines an acousto-optic fiber Bragg grating ("FBG") sensor with a photoacoustic transducer. The imaging guidewire of FIG. 2 includes an optical fiber assembly 105 and an optical fiber transducer 100, e.g., a strain-detecting Fabry-Perot interferometric sensor, having a first (partially reflective) FBG 110A and a second (substantially fully reflective) FBG 110B. The optical fiber transducer 100 senses acoustic energy received from a nearby region to be imaged, and transduces the received acoustic energy into an optical signal within optical fiber assembly 105. In the example of FIG. 2, the optical fiber transducer 100 includes FBGs 110A-B in an optical fiber core 115 surrounded by an optical fiber cladding 120. FBGs 110A-B are separated by a strain sensing region 125, which, in one example, is about a millimeter in length. This example senses strain by detecting an "optical displacement" between these gratings 110A-B.

An FBG can be conceptualized as a periodic change in the optical index (which is inversely proportional to the speed of light in the material) of a portion of the optical fiber core 115. Light of a specific wavelength traveling down such a portion of core 115 will be reflected; the period (distance) 130 of the change in the optical index determines the particular wavelength of light that will be reflected. The degree of index change and the length 135 of the grating determine the ratio of light reflected to that transmitted through the grating.

In the example shown in FIG. 2, the distal portion of the imaging guidewire combines an acouso-optic transducer 100 with a photoacoustic transducer 225. The photoacoustic transducer 225 of the distal portion of the imaging guidewire in FIG. 2 includes a single, ultrasound transmit section. The photoacoustic transducer 225 includes a blazed Bragg grating 230. In the illustrative example of FIG. 2, blazed Bragg grating 230 is implemented in the strain sensitive region of the optical fiber transducer 100, between FBGs 110A-B. Unlike an unblazed Bragg grating, which typically includes impressed index changes that are substantially perpendicular to the longitudinal axis of the fiber core 115 of the optical fiber 105, the blazed Bragg grating 230 includes obliquely impressed index changes that are at a nonperpendicular angle (the "blaze" angle) to the longitudinal axis of the optical fiber assembly 105.

A standard unblazed FBG partially or substantially fully reflects optical energy of a specific wavelength traveling down the axis of the fiber core 115 of optical fiber 105 back up the same axis. Blazed FBG 230 reflects this optical energy away from the longitudinal axis of the optical fiber 105. For a particular combination of blaze angle and optical wavelength, the optical energy will leave blazed FBG 230 substantially normal (i.e., perpendicular) to the longitudinal axis of the optical fiber 105.

In the illustrative example of FIG. 2, an optically absorptive photoacoustic material 235 is placed on the surface of optical fiber 105. The optically absorptive photoacoustic material 235 is positioned, with respect to the blazed grating 230, so as to receive the optical energy leaving the blazed grating. The received optical energy is converted in the optically absorptive material 235 to heat that expands the optically absorptive photoacoustic material 235. The optically absorptive photoacoustic material 235 is selected to expand and contract quickly enough to create and transmit an ultrasound or other acoustic wave that is used for acoustic imaging of the region of interest about the distal tip (or other desired portion) of the imaging guidewire.

Blazed Bragg grating 230 receives light that for transmit purposes may be in the form of a short pulse from a proximal end of fiber core 115, and directs the received light outward through photoacoustic material 235, which creates and transmits an ultrasound or other acoustic wave. The transmitted wave reflects off of a nearby area to be image, e.g., tissue of or in a body lumen, and is received by the sensing region 125, which converts the received wave to an optical signal. The interaction of the reflected acoustic wave with the sensing region 125 changes the apparent optical phase between FBGs 110A and 110B, which leads to a subtle change in the wavelength of the resonance between them. The resulting change in wavelength or intensity is monitored by interface optoelectronics coupled to a proximal end of optical fiber assembly 105.

Using various techniques of this disclosure and as described in more detail below, an imaging guidewire, e.g., intravascularly-deliverable, can include multiple, independent, ultrasound transmit sections within a Fabry-Perot interferometric sensor. Each of the transmit sections within the optical cavity may be addressed using a pulsed fiber transmit laser, e.g., using blazed FBGs. Blazed FBGs within the optical cavity may be tuned to different wavelengths. Tuning the wavelength of the transmit laser to a specific wavelength may cause the laser to resonate and interact with a specific transmit section, e.g., blazed FBG. Images of the vessel may be generated by acquiring information about a first slice of the vessel associated with a first transmit section of a first optical fiber, tuning the wavelength of the transmit laser to resonate with a second transmit section of the first optical fiber, acquiring information about a second slice associated with the second transmit section of the first optical fiber, and so forth, for a number of slices, e.g., ten slices. This process is repeated for a second optical fiber, a third optical fiber, etc. of the imaging guidewire. The acquired information about the slices from each of the optical fibers can then be combined to form a 3D image of the body lumen, e.g., vessel.

Figure 3:
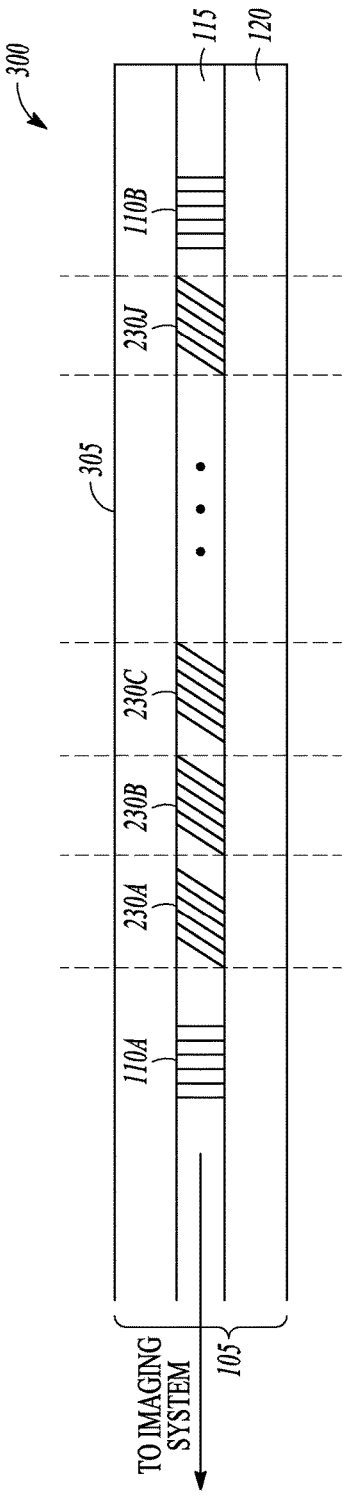
FIG. 3 is a cross-sectional side view illustrating generally one example of a distal portion of an imaging guidewire that includes a Fabry-Perot interferometric sensor that may be used to provide imaging of a body lumen, in accordance with various techniques of this disclosure.

FIG. 3 is a cross-sectional side view illustrating generally one example of a distal portion of an imaging guidewire 300 that includes an intravascularly-deliverable Fabry-Perot interferometric sensor 305 that may be used to provide imaging of a body lumen, in accordance with various techniques of this disclosure. For example, the sensor 305 may be used to provide 3D imaging of a body lumen. In other example implementations, the sensor 305 may be used to provide 2D imaging. As seen in FIG. 3, the sensor 305 includes a pair of FBGs, namely FBG 110A and 110B. In contrast to the device shown in FIG. 1, multiple blazed Bragg gratings 230A-230J (collectively "blazed gratings 230") are positioned between the pair of FBGs that form the Fabry-Perot interferometric sensor 305. Each of the multiple blazed Bragg gratings 230 (or "transmit gratings") may be configured to resonate at a different wavelength. As such, each transmit grating may be separately addressable by tuning a laser to transmit at a wavelength corresponding to that of the particular transmit grating. By tuning the wavelength of the transmit laser to a specific wavelength, the laser will only resonate and interact with a particular transmit grating. In accordance with this disclosure, a plurality of the transmit gratings can be separately addressed by a transmit laser and a plurality of slices of the body lumen, e.g., vessel, artery, etc., can be acquired that each correspond to a respective transmit grating.

By way of specific example, the blazed Bragg grating 230A may be configured to resonate at a first wavelength, $\lambda_1$. A transmit laser may be tuned to transmit at the first wavelength, $\lambda_1$. The optical energy associated with wavelength $\lambda_1$ travels down the axis of the fiber core of the optical fiber assembly 105 and resonates only with the blazed Bragg grating 230A. As such, the blazed Bragg grating 230A decouples the optical energy from the core and reflects the optical energy substantially normal (e.g., perpendicular) to the longitudinal axis of the optical fiber assembly 105 out of the cladding and into the absorptive photoacoustic material (not depicted). A receive laser configured to resonate with FBGs 110A-B (or the "receive gratings") senses the strain by detecting an optical displacement between the receive gratings. Using this acquired information, an image of a first slice of a body lumen, e.g., a vessel, having a length of the blazed Bragg grating 230A, e.g., 1 mm, may be generated.

Continuing with the example from above, the blazed Bragg grating 230B may be configured to resonate at a second wavelength, $\lambda_2$. The transmit laser may be tuned to transmit at the second wavelength, $\lambda_2$. The optical energy associated with wavelength $\lambda_2$ travels down the axis of the fiber core of the optical fiber assembly 105 and resonates only with the blazed Bragg grating 230B. As such, the blazed Bragg grating 230B decouples the optical energy from the core and reflects the optical energy substantially normal (e.g., perpendicular) to the longitudinal axis of the optical fiber assembly 105 out of the cladding and into the absorptive photoacoustic material (not depicted). The receive laser configured to resonate with FBGs 110A-B senses the strain by detecting an optical displacement between these gratings 110A-B. Using the acquired information, an image of a second slice of a body lumen, e.g., a vessel, having a length of the blazed Bragg grating 230B, e.g., 1 mm, may be generated.

Figure 4A:
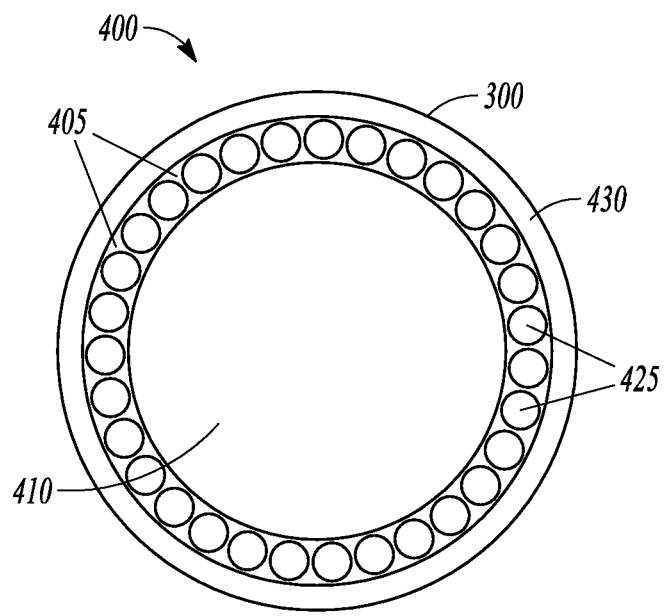
FIG. 4A is a schematic diagram that illustrates generally one example of a cross-sectional end view of a proximal portion of a guidewire.
Figure 4B:
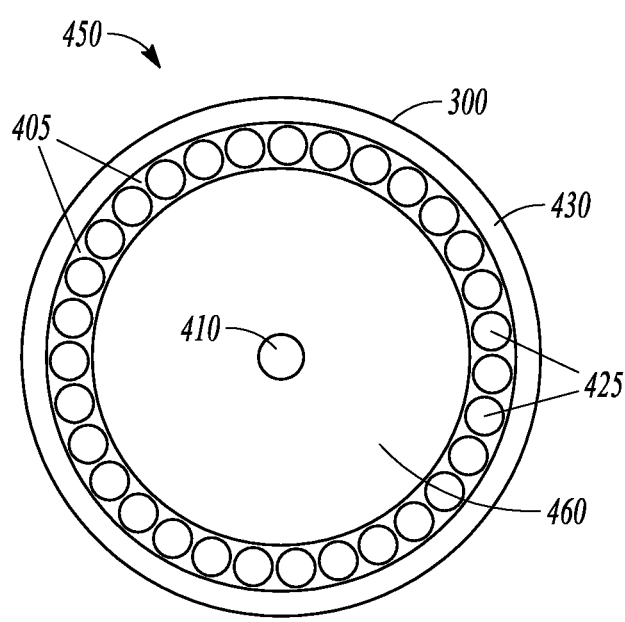
FIG. 4B is a schematic diagram that illustrates generally one example of a cross-sectional end view of a distal portion of a guidewire.

Using these techniques, each of the blazed Bragg gratings 230A-230J of a first optical fiber can be addressed by tuning the transmit laser to the particular wavelength associated with a blazed Bragg grating. By knowing the wavelength of the transmit laser at a particular time, the physical position of the blazed Bragg grating 230A-230J may be determined. Images of slices of a body lumen associated with the blazed Bragg gratings 230A-230J of a first optical fiber may be generated using the acquired information. This process is repeated for a second optical fiber, a third optical fiber, etc. disposed about a circumference of the imaging guidewire (as shown in FIGS. 4A and 4B). The acquired slices from each of the optical fibers can then be organized and combined to form a 3D image of the body lumen, e.g., vessel. The 3D image of the body lumen may have a length equal to the sum of the lengths of the individual blazed Bragg gratings 230A-230J. In other example implementations, a single sensor 305 may be used to provide 2D imaging, e.g., of a body lumen.

In some example configurations, there may be ten blazed Bragg gratings on each optical fiber, e.g., blazed Bragg gratings 230A-230J of FIG. 3. If each blazed Bragg grating 230 is 1 mm long, then the imaging guidewire 300 may generate a 3D image having a length of 10 mm. In other example configurations, there may be twenty blazed Bragg gratings 230 on each optical fiber. If each blazed Bragg grating 230 is 1 mm long, then the imaging guidewire 300 may generate a 3D image having a length of 20 mm. A blazed Bragg grating 230 may have a length greater than 1 mm or less than 1 mm. In other configurations, there may be less than ten blazed Bragg gratings, or more than ten or twenty blazed Bragg gratings.

FIG. 4A is a schematic diagram that illustrates generally one example of a cross-sectional end view of a proximal portion 400 of imaging guidewire 300, which includes guidewire core 410, a plurality of coated optical fibers 425, e.g., 32 optical fibers, binder material 405, and outer coating 430. In this example, but not by way of limitation, the diameter of the core 410 is about 11/1000 inch, the diameter of the optical fibers 425 is about (1.25)/1000 inch, and the optional outer coating 430 is about (0.25)/1000 inch thick.

FIG. 4B is a schematic diagram that illustrates generally one example of a cross-sectional end view of distal portion 450 of imaging guidewire 300, e.g., adjacent to a distal tip. In this example, but not by way of limitation, the diameter of core 410 has tapered down to about (4.0)/1000 inch, circumferentially surrounded by a void 460 of about the same diameter (e.g., about 11/1000 inch) as the core 410 near the proximal end of the imaging guidewire 300. In this example, the optical fibers 425 are circumferentially disposed in the binder material 405 around the void 460. Binder material 405 provides structural support. Optical fibers 425 are optionally overlaid with the outer coating 430. Alternatively, a support structure (not shown) may be included within the void to preserve the shape of the fiber optic circumferential assembly.

As indicated above, the distal portions of a plurality of the optical fibers 425 may each be configured to include an acousto-optic fiber Bragg grating ("FBG") sensor 305 that includes multiple, independent, transmit blazed Bragg gratings positioned between a pair of receive Bragg gratings, as shown and described above with respect to FIG. 3. These circumferentially offset sensors 305 may each acquire information about a plurality of slices that can be organized and combined to form a 3D image of the body lumen, for example.

Figure 5:
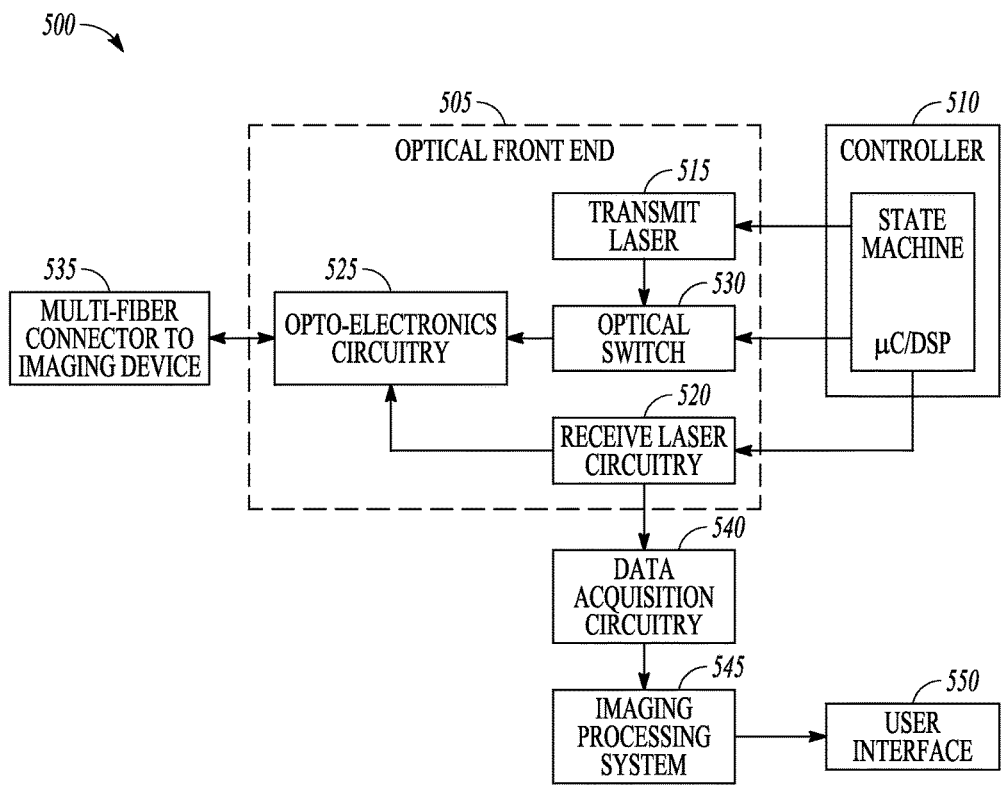
FIG. 5 is a block diagram illustrating generally one example of a system for producing images of a body lumen, in accordance with this disclosure.

FIG. 5 is a block diagram illustrating generally one example of a system 500 for producing 3D images of a body lumen, in accordance with this disclosure. The system 500 may include an optical front end 505 that may be controlled by a controller 510. The controller 510 may be a timing and control module that may include a state machine and/or a microcontroller. Among other things and as described in more detail below, the controller 510 may be configured to control the wavelength of a transmit laser 515 and tune the wavelength of one or more receive lasers.

The optical front end 505 may include a tunable transmit laser 515, receive laser circuitry 520, opto-electronics circuitry 525, and optical switch circuitry 530. The tunable transmit laser 515 may be configured to emit light at a plurality of wavelengths in order to resonate with a plurality of transmit gratings 230 on the sensor 305 (FIG. 3). In some example configurations, the transmit laser 515 may be a high power pulsed laser. An output of the transmit laser may be coupled to the optical switch circuitry 530.

The tunable transmit laser 515 is used for providing light to the imaging guidewire 300 for the transmitted ultrasound. A separate receive laser of the receive laser circuitry 520 is used for providing light to the imaging guidewire 300 for being modulated by the received ultrasound.

As indicated above, the optical front end 505 may include optical switch circuitry 530. The optical switch circuitry 530 may be configured to receive and switch an output of the transmit laser 515 to any one of the optical fibers, e.g., one of 32 optical fibers, of the imaging guidewire 300 (FIGS. 4A and 4B). In one example implementation, the optical switch circuitry 530 may be designed to accommodate high optical powers at a fast switching rate. For example, the optical switch circuitry 530 may be able to switch from one optical fiber to another in about a microsecond.

The receive laser circuitry 520 may include a plurality of receive lasers, e.g., 32 receive lasers. For example, if the imaging guidewire 300 includes 32 optical fibers 425 that each include a sensor 305, then 32 receive lasers may be needed. Thus, in one example configuration, the system 500 may include a single tunable transmit laser 515 that may be configured to address each blazed Bragg grating on each of the optical fibers, and 32 receive lasers.

The receive laser circuitry 520 may include a low noise current driver and active noise reduction capabilities (described in more detail below with respect to FIG. 6). In addition, the receive laser circuitry 520 may include temperature control capabilities. For example, a user or the controller 510, may adjust the wavelength of a receive laser of the receive laser circuitry 520 by adjusting a drive current of a thermoelectric cooler (TEC) of a receive laser (e.g., to control large shifts in wavelength), which can alter the temperature of a submount of the receive laser. To control small shifts in wavelength, a user or the controller 510 may adjust the drive current of the receive laser itself.

The receive laser circuitry 520 may also include photodiodes for receiving the optical signals and converting the received optical signals to an electronic signal, e.g., radiofrequency (RF) signal, that can be filtered, e.g., via band-pass filters, to acquire an electrical signal within a desired frequency range.

In addition, the receive laser circuitry 520 may include a laser tracking circuit to track a position on a slope of a transmission notch. An example of a laser tracking circuit is described in detail in U.S. patent application Ser. No. 13/902,334, titled "OPTICAL FIBER PRESSURE SENSOR GUIDEWIRE," to Eberle et al., and filed on May 24, 2013, the entire content of which being incorporated herein by reference. Reflections from FBG 110A interfere with reflections from FBG 110B because of the phase shift between FBGs 110A-B. As a result, a narrow transmission notch is created within a reflection band. As described in detail in U.S. patent application Ser. No. 13/902,334, a wavelength of a narrow band laser (in relation to the wavelength response of FBGs 110A-B) can be locked on a point on a slope of the narrow transmission notch, e.g., at about 50% of the depth of the notch. As the temperature changes, the notch shifts and, consequently, the point on the slope shifts. The tracking circuit can then track the locked point on the slope and a change in temperature can be determined from its change in position. Then, the tracking circuit can measure the change in wavelength and, in response, alter the laser's operating characteristics, e.g., drive current.

In some example configurations, the tunable transmit laser 515 and the receive laser(s) may be set at two different wavelengths, e.g., in two different wavelength bands. For example, the transmit laser 515 may be tuned to a wavelength of about 1060 nanometers (nm), which is based upon the particular blazed Bragg grating 230 and the slice to be imaged, and the receive laser may be tuned to a wavelength of about 1550 nm, which is based upon the wavelength of the pair of FBGs 110A-B forming the Fabry-Perot interferometer. Because of the large difference in wavelength, the transmit laser 515 and a receive laser are coupled into the same optical fiber by means of an optical multiplexer before being directed to the imaging device.

The opto-electronics circuitry 525 may include a transmit/receive (T/R) multiplexer configured to combine the two different wavelengths of the transmit laser and the receive laser onto a single fiber, e.g., to reduce cost and system complexity. The transmit laser 515 transmits light on a first optical fiber, a receive laser transmits light to be modulated by the received ultrasound on a second fiber, and the T/R multiplexer combines the output onto a single fiber that includes both wavelengths. Additional information regarding multiplexing techniques may be found in Bates.

The opto-electronics circuitry 525 may include a polarization controller. The polarization controller may be used to overcome the effects of birefringence and determine a true reading. The slope of the resonant features (or the transmission notch) and the Full-Width Half-Maximum (FWHM) of the resonant features become much steeper and narrower, respectively, for longer Fabry-Perot interferometric sensors, such as sensor 305 shown in FIG. 3. As such, it may be desirable to account for the effects of optical birefringence and ultrasound induced birefringence (UIB).

The first effect, optical birefringence, may occur when light of different polarizations is subject to small variations in the effective refractive index. The wavelength of a Fabry-Perot interferometer is set by the combination of the physical spacing of the fringes in the FBGs and the effective refractive index. If different polarizations see slightly different refractive indices, then they will see a slightly different wavelength for the resonant features. This difference is very small but, in the context of a device such as sensor 305, the difference is significant.

The second effect is UIB, which is dependent on the relative size of the optical fiber and the frequency or wavelength of the ultrasound signal. If the wavelength of the ultrasound signal is significantly larger than the diameter of the optical fiber, then the effect of UIB is minimal. But, if the optical fiber diameter and the ultrasound wavelength are of the same order, then higher order mechanical modes are excited in the fiber which may lead to UIB.

Both optical birefringence and UIB may lead to variations in the perceived signal depending on the polarization of the light that is used to sense the ultrasound and the direction which the ultrasound is incident upon the fiber. In some example configurations, the sensor 305 may have an optical fiber diameter of about 25 micrometers (μm) and the ultrasound may have a wavelength of about 75 μm. In such a configuration, there may be variations in the signal level of several decibels (dB) and also phase shifting of the signal which may degrade the quality of the reconstructed image if not mitigated.

One solution to mitigate the effects of optical birefringence and UIB is to use an optical device to average or scramble the polarization such that the effect is averaged out. The frequency of the scrambling or averaging may be selected such that it is able to provide sufficient averaging for video frame rates but not so high that it has residual effects in the window of imaging frequencies. In some example implementations, the frequency may be above about 30 Hz (e.g., video frame rate) and below about 1 megahertz (MHz)(e.g., ultrasound lower bandwidth).

The polarization scrambling techniques may scramble or average a range of polarization states so the final result is not biased to any given combination of birefringent axis of the FBG and incident polarization state. The polarization scrambling can be implemented by sweeping a series of "optical waveplates" through a pseudo-random pattern with sufficient frequency that the desired signal will be averaged satisfactorily. Optical waveplates are devices that can alter the state of polarization. In order to measure a typical cardiovascular pressure profile with a heart rate of 0 beats per minute to 200 beats per minute, scrambling techniques can average at a rate that is sufficient to capture the dynamic profile, e.g., an effective frequency of several hundred hertz.

The optical waveplates can be physically located between where the laser beam exits a receive laser and the FBGs of the optical fiber sensor 305. In one example, an optical waveplate can be formed by wrapping a portion of the optical fiber around a piezoelectric material and by stretching the fiber upon application of a voltage to the piezoelectric material. In another example, an optical waveguide can be used to form an optical waveplate. The application of a voltage across electrodes built into the optical waveguide can result in the change of the refractive index.

Using these polarization scrambling techniques, it is not necessary to know the levels or patterns of birefringence in the system because the polarization controlling techniques do not rely upon feedback. Instead, the polarization scrambling techniques rely on an averaged polarization that is achieved by sweeping through as many available polarization states to get an average polarization value so the final result is not biased to any given combination of birefringent axis of the FBG and incident polarization state. Additional information regarding how the polarization scrambling techniques are used to determine a true reading are disclosed in U.S. Provisional Application No. 61/709,700, titled "POLARIZATION SCRAMBLING FOR INTRA-BODY FIBER OPTIC SENSOR", to Rourke et al. and filed on Oct. 4, 2012, the entire content of which being incorporated herein by reference.

The system 500 of FIG. 5 may include a connector 535, e.g., a multi-fiber optical connector, configured to connect the optical front end 505 to the imaging guidewire 300. In one example implementation, the connector 535 may be an optical coupler, such as described in Bates.

In addition, the system 500 may include data acquisition circuitry 540 that includes, for example, analog-to-digital converters (ADCs), band-pass filters, and a memory device to store the processed data.

As shown in FIG. 5, the system 500 may include an imaging processing system 545 and a user interface 550. The imaging processing system 550 may be configured to receive filtered and digitized information representing the 2D slices of the imaged area, e.g., body lumen, and include, for example, a controller, and a 3D graphics processor. The controller 510 of the imaging processing system 545 may execute instructions that define an imaging algorithm to generate images from the filtered and digitized information.

The 3D graphics processor of the imaging processing system 545 may generate 3D images from the information generated by the imaging algorithm. The user interface 550 may include a display to display the 3D images generated by the 3D graphics processor. In addition, the user interface 550 may include a keyboard, touchscreen, mouse, and/or other input device(s) to control one or more aspects of the system 500.

By way of specific example, the controller 510 may control the optical switch circuitry 530 to couple the transmit laser 515 to a first one of the optical fibers of the imaging guidewire, and tune the transmit laser 515 to emit an optical signal at a first wavelength that resonates with a first blazed Bragg grating, e.g., blazed Bragg grating 230A of FIG. 3, of the first optical fiber. In one example implementation, the controller 510 may control the transmit laser 515 to fire a number of first optical signals or light pulses, e.g., 200-300 pulses at 50-100 kHz, at the first wavelength. While the transmit laser 515 is transmitting the light pulses, a first one of a plurality of receive lasers, e.g., continuous wave (CW) lasers, may be transmitting an optical signal on another optical fiber that may be modulated by the ultrasound received in response to the firings.

The optical energy of the first optical signal at the first wavelength travels down the fiber core of the first optical fiber and is reflected out of the first optical fiber by the first blazed Bragg grating, e.g., blazed Bragg grating 230A of FIG. 3. The outwardly reflected optical energy impinges on the photoacoustic material 235. The photoacoustic material 235 then generates a responsive acoustic impulse that radiates away from the photoacoustic material 235 toward nearby biological or other material to be imaged in a body lumen. Acoustic energy of a specific frequency is generated by optically irradiating the photoacoustic material 235.

As described above, the strain-detecting Fabry-Perot interferometric sensor 305 senses any acoustic energy received from a nearby region to be imaged, and transduces the received acoustic energy into a responsive second optical signal within the optical fiber. The strain is sensed by detecting an "optical displacement" between FBGs 110A-B.

Next, the controller 510 may control the optical switch circuitry 530 to couple the transmit laser 515 to a second one of the optical fibers of the imaging guidewire, and may control the transmit laser 515 to transmit a third optical signal at the first wavelength that resonates with the first blazed Bragg grating, e.g., blazed Bragg grating 230A of FIG. 2, of the second optical fiber.

The optical energy of the third optical signal at the first wavelength of the transmitted pulses travels down the fiber core of the second optical fiber and is reflected out of the second optical fiber by the first blazed Bragg grating, e.g., blazed Bragg grating 230A of FIG. 3. The photoacoustic material 235 then generates a responsive acoustic impulse that radiates away from the photoacoustic material 235 toward nearby biological or other material to be imaged in a body lumen. The sensor 305 senses any acoustic energy received from the nearby region to be imaged, and transduces the received acoustic energy into a responsive fourth optical signal within the optical fiber.

The controller 510 may continue to control the optical switch circuitry 530 to couple the transmit laser 515 to the optical fibers disposed about the circumference of the imaging guidewire, and control the transmit laser 515 to transmit optical signals at the first wavelength that resonates with the first blazed Bragg grating, e.g., blazed Bragg grating 230A of FIG. 3, of a plurality of the optical fibers. In this manner, the system 500 acquires information about a first 2D slice, or plane, of the region to be imaged that corresponds to each of the first blazed Bragg gratings positioned around the circumference of the imaging guidewire 300.

Each 2D slice, or plane, is defined by a particular wavelength associated with a blazed Bragg grating. The controller 510 may associate the wavelength transmitted by the transmit laser 515 and the time at which the wavelength was transmitted, e.g., using a timestamp, and may store the association in a memory device of the system 500. By knowing which wavelength the transmit laser 515 transmitted and the time at which the wavelength was transmitted, the controller 510 may map the acquired information to certain positions in a particular plane. Later, the system 500 and, in particular, the imaging processing system 545, may organize and combine the 2D slices, which each have a length approximately equal to a respective blazed Bragg grating, to form a 3D image of the imaged region, e.g., a body lumen, which has a length approximately equal to the sum of the lengths of each of the blazed Bragg gratings.

Next, the controller 510 may control the optical switch circuitry 530 to couple the transmit laser 515 to the first one of the optical fibers of the imaging guidewire, and tune the transmit laser 515 to transmit an optical signal at a second wavelength that resonates with a second blazed Bragg grating, e.g., blazed Bragg grating 230B of FIG. 3, of the first optical fiber. The controller 510 may control the transmit laser 515 to transmit a number of light pulses at the second wavelength, and a second one of the plurality of receive lasers may transmit light on another optical fiber that may be modulated by the ultrasound received in response to the firings. The sensor 305 senses any acoustic energy received from the nearby region to be imaged, and transduces the received acoustic energy into an optical signal within the optical fiber.

The controller 510 may continue to control the optical switch circuitry 530 to couple the transmit laser 515 to the optical fibers disposed about the circumference of the imaging guidewire, and control the transmit laser 515 to emit light at the second wavelength that resonates with the second blazed Bragg grating, e.g., blazed Bragg grating 230B of FIG. 3, of a plurality of the optical fibers. In this manner, information about a second 2D slice of the region to be imaged is acquired that corresponds to each of the second blazed Bragg gratings positioned around the circumference of the imaging guidewire 300.

The controller 510 repeats the actions described above to acquire information about a third 2D slice, a fourth 2D slice, a fifth 2D slice, etc. For purposes of conciseness, these actions will not be described in detail again. Using these techniques, information about a number of 2D slices, e.g., 10-20 2D slices, may be acquired.

In this manner, the controller 510 may acquire information circumferentially about the sensor 305, e.g., using blazed Bragg gratings 230A on a plurality of optical fibers, before circumferentially acquiring information at another longitudinal position on the sensor 305, e.g., using blazed Bragg gratings 230B on the plurality of optical fibers. In other example implementations, the controller 510 may acquire information longitudinally along a first optical fiber of the sensor 305, e.g., using blazed Bragg gratings 230A-230J of the first optical fiber, and then acquire information longitudinally along a second optical fiber of the sensor 305, e.g., using blazed Bragg gratings 230A-230J of the second optical fiber. This process can be repeated for third, fourth, etc. optical fibers. For purposes of conciseness and to avoid repetition, these steps will not be described in detail.

As indicated above, the transmit laser 515 may transmit 200-300 light pulses (optical signals) at each blazed Bragg grating 230. Given that the receive lasers are continuously transmitting light, each transmit pulse may modulate the light transmitted by the receive lasers, resulting in a corresponding acquisition of data for each of the 200-300 transmit pulses. In some examples, techniques may be implemented to improve the acquired data, e.g., signal averaging techniques. For example, if 200 transmit pulses result in 200 data samples, these 200 data samples may be averaged to produce a single data sample that may, for example, have less noise than any of the originally acquired data samples, which can be used to generate a portion of a 2D slice.

To reduce noise further, a band-pass filter may be used to reject frequencies outside a range of interest for the averaged data samples. An ADC may be used to convert the filtered signals to a digital representation that can be stored in a memory device and used by the imaging processing system 545 to generate a 3D image.

The imaging processing system 545 may receive the filtered and digitized information representing the 2D slices of the imaged area, e.g., body lumen. As indicated above, the controller 510 of the system 500 may map the acquired information to certain positions in a particular plane. The controller 510 of the imaging processing system 545 may execute instructions that define an imaging algorithm to organize and combine the mapped information.

The 3D graphics processor of the imaging processing system 545 may generate 3D images from the information generated by the imaging algorithm. The user interface 550 may include a display to display the 3D images generated by the 3D graphics processor. In addition, the user interface 550 may include a keyboard, touchscreen, mouse, and/or other input device(s) to control one or more aspects of the system 500.

For longer Fabry-Perot interferometric sensors, such as sensor 305 shown in FIG. 3, the Free Spectral Range (FSR) is made smaller, which means that the resonant features are more closely spaced. As long as the optical loss of the cavity does not significantly increase, the finesse of the cavity (defined as FSR/FWHM) will remain the same. That is, the slope of the features will increase in the same ratio as the increase in length. This means that the theoretical signal level for a given ultrasound energy incident on the grating will remain the same, which is important when considering the signal-to-noise ratio (SNR).

If the sensor, e.g., sensor 305 of FIG. 3, receives ultrasound from a slice of the cavity, the ultrasound will induce a certain phase change in the cavity. In principal, the strength of the signal will remain the same because it is a function of the slope of the transmission notch and the optical phase change caused by the ultrasound. For longer cavities, the absolute wavelength shift will be less (optical phase change multiplied by FSR), but because the slope of the feature is steeper, the signal will be the same. The noise floor, however, may be higher due to the steeper slope because the noise is dependent on the amount of laser phase noise (or linewidth) multiplied by the slope of the feature. This may lead to an overall loss in SNR if the phase noise (or linewidth) of the laser multiplied by the slope is larger than the shot noise limit. To improve upon this loss, noise subtraction techniques may be utilized to recover the lost SNR, as described below.

As the optical cavity is stretched to include multiple blazed Bragg gratings, additional noise may be introduced into the system. For example, laser linewidth noise may be increased. A laser emits photons, with each photon having an energy that defines the photon's wavelength. The energy of a photon is defined by Equation (1):

$$E=hc/\lambda, \quad (1)$$

where E is the energy of the photon, h is Planck's constant, c is the speed of light, and $\lambda$ is wavelength.

Theoretically, a laser emits only photons of the same wavelength and thus would be perfectly monochromatic. In reality, however, there are no perfectly monochromatic lasers. Rather, lasers emit photons of varying energy levels and thus varying wavelengths.

This variation in wavelength in the emitted laser light may directly impact the noise in the system. For example, a change in the laser in the megahertz (MHz) region may translate into noise in the MHz region of the ultrasound detected by an imaging guidewire. It is very difficult to distinguish the part of the signal that is true ultrasound from the apparent signal that is linewidth noise, which may lead to noise limited performance in the case of very small ultrasound signals. As described below, the laser linewidth noise may be reduced or eliminated using various noise subtraction techniques.

The noise subtraction scheme is based on a reference cavity with similar optical characteristics to the Fabry-Perot cavity that forms the ultrasound receiver. The general operating principal is to demodulate the noise caused by the phase noise or linewidth of the laser into an electrical signal that can then be subtracted from the signal from the ultrasound receiver.

Figure 6:
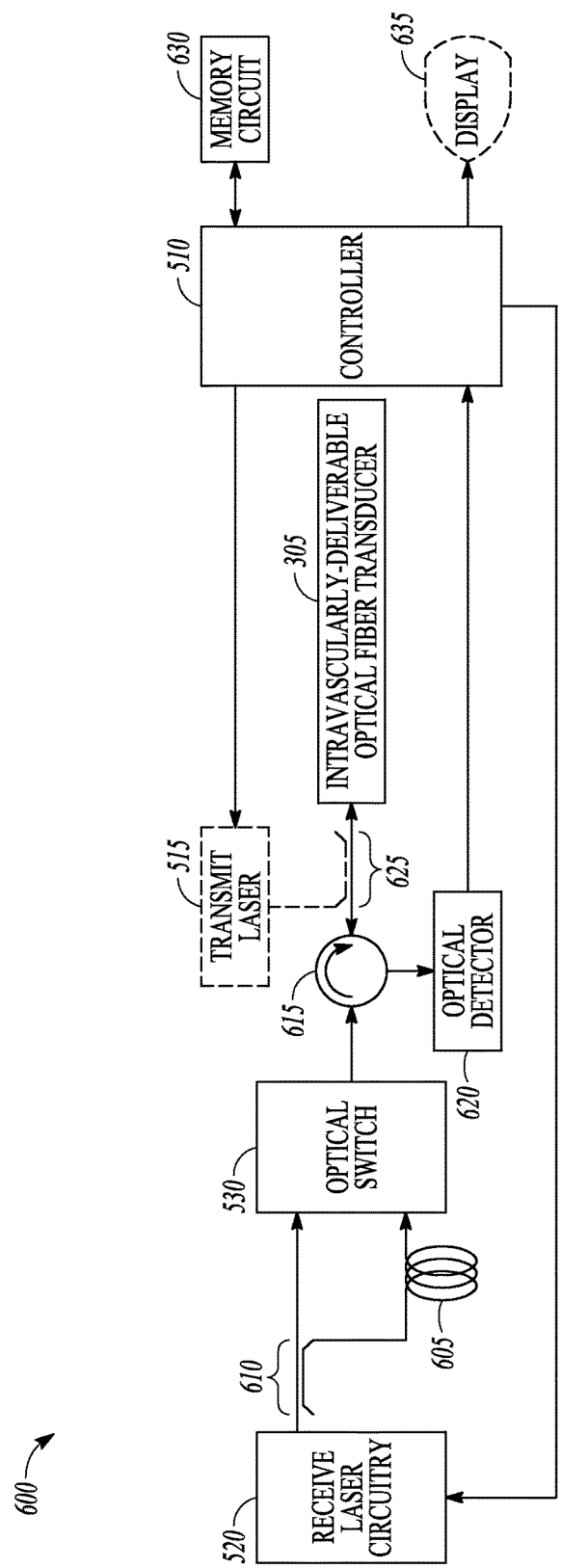
FIG. 6 is a block diagram illustrating generally one example of a system that incorporates noise subtraction techniques.

FIG. 6 is a block diagram illustrating generally one example of a system 600 that incorporates noise subtraction techniques. The system 600 can include an intravascularly-deliverable optical fiber sensor 305 and an optical delay line 605. The system 600 can include the receive laser circuitry 520, such as coupled to an optical switch 530. A receive laser of the receive laser circuitry 520 can be coupled to a first input of the switch 530 bypassing the optical delay line 605, or coupled through the delay line 605 to a second input of the switch 530, such as using a splitter/combiner 610. An output of the switch 530 can be coupled to an optical circulator 615.

In an illustrative example, the specified optical propagation delay of the optical delay line 605 can be about 6 microseconds ($\mu$s), such as corresponding to an optical fiber length of about 1.2 kilometers (km). A latency of the 2:1 switch 220 can be about 1 $\mu$s or less.

Optical energy reflected from the intravascularly-deliverable optical fiber transducer 305 can be coupled to an optical detector 620. The tunable transmit laser 515 can provide optical energy to the optical fiber sensor 305 such as using a splitter/combiner 625 (e.g., output from the receive laser circuitry 520 and the transmit laser 515 can be wavelength-division-multiplexed (WDM)). Such optical energy from the transmit laser 515 can be converted to an acoustic transmit pulse to elicit reflection of acoustic energy from structures in a tissue region nearby an acoustically-emitting portion of the sensor 305. Such reflections can be converted from optical to electrical signals using the optical detector 620, such as for processing by the controller 510, or storage in a memory circuit 630. An image or other information indicative of the optical energy reflected from the optical sensor 305 can be presented to a user, such as using a display 635.

An instance of optical energy from the receive laser of the receive laser circuitry 520 can be coupled to both the optical switch 530, and to the delay line 605. In this manner, a time-domain phase noise signature from the receive laser of receive laser circuitry 520 can be obtained during respective first and second durations. In an example, such as during the first duration, the instance of optical energy from the receive laser of receive laser circuitry 520 can be presented to the sensor 305 during or shortly after a "transmit pulse" from the transmit laser 515. During a second duration, the instance of optical energy from the receive laser of receive laser circuitry 520 can be delayed for a specified duration by the optical delay line 605, and then presented to the sensor 305, such as without a corresponding transmit pulse. In this manner, during the second duration, the reflected optical energy can be less modulated or un-modulated by vibration, stress, or strain, and can provide information indicative primarily of the phase noise of the receive laser of receive laser circuitry 520. The first and second durations need not occur in any particular order. For example, a transmit pulse can be suppressed during the first duration, the phase noise signature can be obtained, and the transmit pulse can be enabled shortly before or during the second duration.

Phase noise signature information determined during the second duration can then be subtracted from the information determined during the first duration, thereby producing a noise-mitigated signal. Additional information regarding this noise subtraction technique and other noise subtraction techniques is described in detail in U.S. Provisional Application No. 61/737,299, titled "NOISE SUBTRACTION FOR INTRA-BODY FIBER OPTIC SENSOR", to Eberle et al. and filed on Dec. 14, 2012, the entire content of which being incorporated herein by reference.

Figure 7:
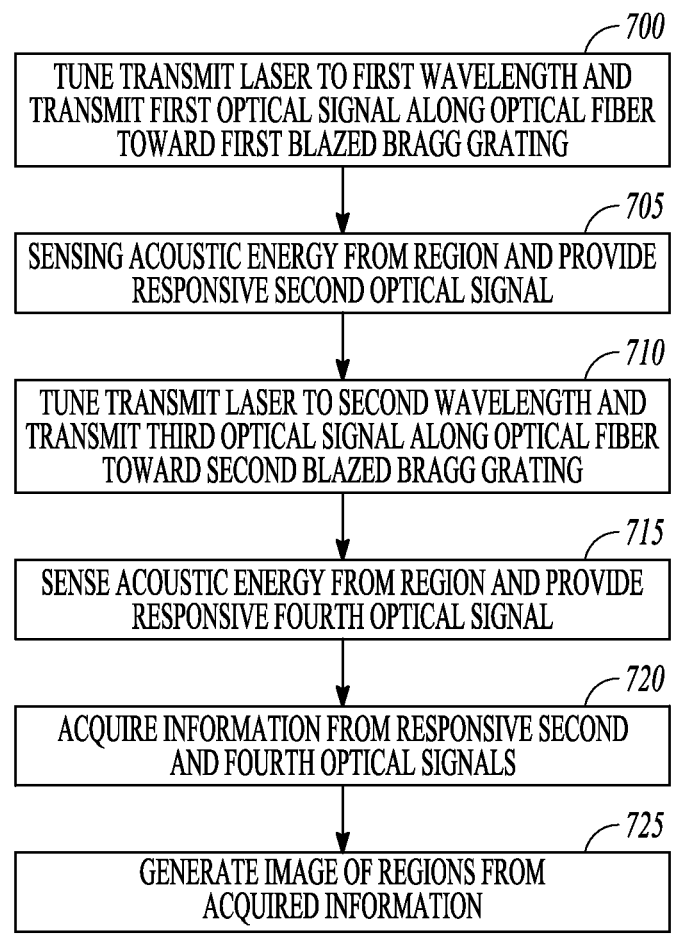
FIG. 7 is a flow chart depicting an example method implementing various techniques of this disclosure.

FIG. 7 is a flow chart depicting an example method implementing various techniques of this disclosure. In the example method of FIG. 7, the controller 510 may tune the transmit laser 515 to a first wavelength and may control the transmit laser 515 to transmit a first optical signal along an optical fiber toward a first blazed Bragg grating of the sensor, e.g., blazed Bragg grating 230A of the sensor 305, which is configured to generate acoustic energy for imaging a first region in response to the first optical signal (700). An interferometer of the sensor 305 that includes a first FBG and a second FBG, e.g., FBGs 110A-B of sensor 305, may sense acoustic energy from the region and, using receive laser circuitry 520, may provide a responsive second optical signal (705).

Then, the controller 510 may tune the transmit laser 515 to a second wavelength and may control the transmit laser 515 to transmit a third optical signal along the optical fiber toward a second blazed Bragg grating of the sensor, e.g., blazed Bragg grating 230B of the sensor 305, which is configured to generate acoustic energy for imaging a second region in response to the third optical signal, where the first and second blazed Bragg gratings are positioned between the first and second FBGs of the interferometer (710). The interferometer of the sensor 305 may sense acoustic energy from the second region and, using receive laser circuitry 520, may provide a responsive fourth optical signal (715). The system 500, e.g., data acquisition circuitry 540, may acquire information from the responsive second and fourth optical signals (720). The system 500, e.g., imaging processing system 545, may generate an image of the first and second regions from the acquired information (725).

In some example configurations, the generated image may be displayed, e.g., on a display of user interface 550. In one example configuration, prior to generating the image, the system 500 may generate different polarization states using a polarization scrambler so the final result is not biased to any given combination of birefringent axis of the FBG and incident polarization state.

In another example configuration, noise subtraction techniques may be used to reduce or eliminate phase noise. For example, prior to generating the image, the system 500 may obtain first phase noise information during a first duration and second phase noise information during a second duration, and then subtract the second phase noise information from the first phase noise information.

Figure 8:
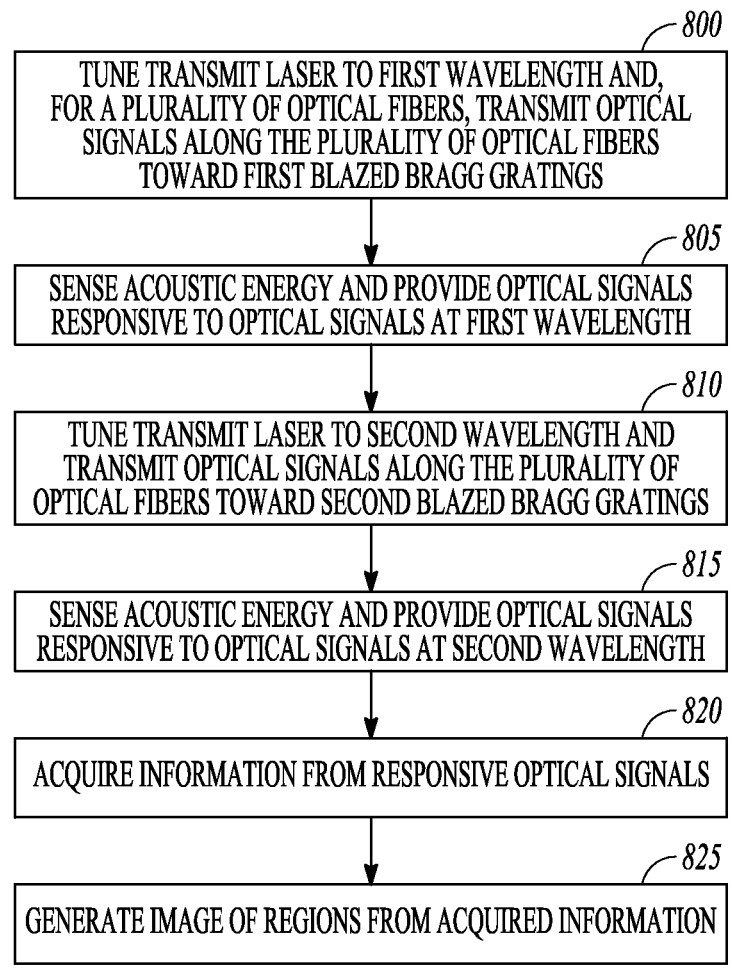
FIG. 8 is a flow chart depicting another example method implementing various techniques of this disclosure.

FIG. 8 is a flow chart depicting another example method implementing various techniques of this disclosure. In the example method of FIG. 8, the controller 510 may tune the transmit laser 515 to a first wavelength and, for a plurality of optical fibers, may control the transmit laser 515 and the optical switch 530 to sequentially transmit first optical signals along the plurality of optical fibers toward first blazed Bragg gratings on each of the plurality of optical fibers, e.g., blazed Bragg gratings 230A of the sensor 305, to generate acoustic energies for imaging first regions in response to the first optical signals (800). Respective interferometers associated with each sensor of the plurality of optical fibers may sense acoustic energy and, using receive laser circuitry 520, may provide respective second optical signals responsive to the sequentially transmitted first optical signals (805).

Then, the controller 510 may tune the transmit laser 515 to a second wavelength and, for a plurality of optical fibers, may control the transmit laser 515 and the optical switch 530 to sequentially transmit third optical signals along the plurality of optical fibers toward second blazed Bragg gratings on each of the plurality of optical fibers, e.g., blazed Bragg grating 230B of the sensor 305, to generate acoustic energies for imaging first regions in response to the third optical signals (810). Respective interferometers associated with each sensor of the plurality of optical fibers may sense acoustic energy and, using receive laser circuitry 520, may provide respective fourth optical signals responsive to the sequentially transmitted optical signals (815).

The above actions may be repeated for each of the desired blazed Bragg gratings of the sensor 305, e.g., blazed Bragg gratings 230C-230J.

The system 500, e.g., using data acquisition circuitry 540, may acquire information from the responsive optical signals (820) and generate e.g., using imaging processing system 545, an image of the 2D slices, e.g., regions, from the acquired information (825). More particularly and as described above, the controller 510 may associate the wavelength transmitted by the transmit laser 515 and the time at which the wavelength was transmitted, e.g., using a timestamp, and may store the association in a memory device of the system 500. By knowing which wavelength the transmit laser 515 transmitted and the time at which the wavelength was transmitted, the controller 510 may map the acquired information to certain positions in a particular plane. Later, the system 500 and, in particular, the imaging processing system 545, may organize and combine the 2D slices, which each have a length approximately equal to a respective blazed Bragg grating, to form a 3D image of the imaged region, e.g., a body lumen, which has a length approximately equal to the sum of the lengths of each of the blazed Bragg gratings.

In some example configurations, the generated image may be displayed, e.g., on a display of user interface 550. In one example configuration, prior to generating the image, the system 500 may generate different polarization states using a polarization scrambler so the final result is not biased to any given combination of birefringent axis of the FBG and incident polarization state.

In another example configuration, noise subtraction techniques may be used to reduce or eliminate phase noise. For example, prior to generating the image, the system 500 may obtain first phase noise information during a first duration and second phase noise information during a second duration, and then subtract the second phase noise information from the first phase noise information.

Additional Notes and Examples

Example 1 is directed to a sensor positioned on an elongate optical fiber, the sensor including a plurality of blazed Bragg gratings configured to generate acoustic energy for imaging a region in response to a first optical signal, an interferometer configured to sense acoustic energy from the region and to provide a responsive second optical signal, the interferometer including a first fiber Bragg grating (FBG) and a second FBG, wherein the plurality of blazed Bragg gratings are positioned between the first and second FBGs.

In Example 2, the sensor of Example 1 can include, wherein each of the plurality of blazed Bragg gratings is configured to resonate at a respective wavelength.

In Example 3, the sensor of any one or more of Examples 1 to 2 can include, wherein the plurality of blazed Bragg gratings includes 2-20 blazed Bragg gratings.

In Example 4, the sensor of any one or more of Examples 1 to 3 can include, wherein the plurality of blazed Bragg gratings includes more than 20 blazed Bragg gratings.

In Example 5, the sensor of any one or more of Examples 1 to 4 can include a photoacoustic material.

Example 6 is directed to an imaging guidewire. The imaging guidewire can include an elongate guidewire core, including proximal and distal portions and a substantially cylindrical circumference; an elongate optical fiber located along a length of the guidewire core, the elongate optical fiber including a sensor positioned at the distal portion, the sensor including: a plurality of blazed Bragg gratings configured to generate acoustic energy for imaging a region in response to a first optical signal, an interferometer configured to sense acoustic energy from the region and to provide a responsive second optical signal, the interferometer including a first fiber Bragg grating (FBG) and a second FBG, wherein the plurality of blazed Bragg gratings are positioned between the first and second FBGs.

In Example 7, the imaging guidewire of Example 6 can include, wherein each of the plurality of blazed Bragg gratings is configured to resonate at a respective wavelength.

In Example 8, the imaging guidewire of any one or more of Examples 6 to 7 can include, wherein the elongate body is substantially cylindrical.

In Example 9, the imaging guidewire of any one or more of Examples 6 to 8 can include, wherein the elongate body includes a plurality of optical fibers, disposed about its cylindrical circumference, wherein the sensor includes a plurality of sensors, and wherein at least some of the plurality of optical fibers each include one of the plurality of sensors.

In Example 10, the imaging guidewire of any one or more of Examples 6 to 9 can include, wherein the plurality of blazed Bragg gratings includes 2-20 blazed Bragg gratings.

In Example 11, the imaging guidewire of any one or more of Examples 6 to 10 can include, wherein the plurality of blazed Bragg gratings includes more than 20 blazed Bragg gratings.

Example 12 is directed to a method that can include tuning a transmit laser to a first wavelength and, for a plurality of optical fibers, transmitting first optical signals along the plurality of optical fibers toward first blazed Bragg gratings configured to generate acoustic energies for imaging first regions in response to the first optical signals; sensing acoustic energies from the first regions and providing responsive second optical signals; tuning the transmit laser to a second wavelength and, for the plurality of optical fibers, transmitting third optical signals along the plurality of optical fibers toward second blazed Bragg gratings configured to generate acoustic energies for imaging second regions in response to the third optical signals; sensing acoustic energies from the second regions and providing responsive fourth optical signals; acquiring information from the responsive second and fourth optical signals; and generating an image of the first and second regions from the acquired information.

In Example 13, the method of Example 12 can include displaying the generated image on a display.

In Example 14, the method of any one or more of Examples 12 to 13 can include, prior to generating the image, generating different polarization states using a polarization scrambler.

In Example 15, the method of any one or more of Examples 12 to 14 can include, prior to generating the image, obtaining first phase noise information during a first duration and second phase noise information during a second duration; and subtracting the second phase noise information from the first phase noise information.

Example 16 is directed to method that can include tuning a transmit laser to a first wavelength and transmitting a first optical signal along an optical fiber toward a first blazed Bragg grating configured to generate acoustic energy for imaging a first region in response to the first optical signal; sensing, using an interferometer including a first fiber Bragg grating (FBG) and a second FBG, acoustic energy from the region and providing a responsive second optical signal; tuning the transmit laser to a second wavelength and transmitting a third optical signal along the optical fiber toward a second blazed Bragg grating configured to generate acoustic energy for imaging a second region in response to the third optical signal, wherein the first and second blazed Bragg gratings are positioned between the first and second FBGs; sensing, using the interferometer, acoustic energy from the second region and providing a responsive fourth optical signal; acquiring information from the responsive second and fourth optical signals; and generating an image of the first and second regions from the acquired information.

In Example 17, the method of Example 16 can include displaying the generated image on a display.

In Example 18, the method of any one or more of Examples 16 to 17 can include, prior to generating the image, generating different polarization states using a polarization scrambler.

In Example 19, the method of any one or more of Examples 16 to 18 can include, prior to generating the image, obtaining first phase noise information during a first duration and second phase noise information during a second duration; and subtracting the second phase noise information from the first phase noise information.

Each of these non-limiting examples described above may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The invention claimed is:

1. A method comprising:
tuning a pulsed transmit laser to a first wavelength and transmitting first optical signals;
switching, using an optical switch circuit, the first optical signals from the pulsed transmit laser to at least a first one of a plurality of optical fibers toward first blazed Bragg gratings configured to generate acoustic energies for imaging first regions in response to the first optical signals;
sensing acoustic energies from the first regions and providing responsive second optical signals,
tuning the pulsed transmit laser to a second wavelength and transmitting third optical signals;
switching, using the optical switch circuit, the third optical signals from the pulsed transmit laser to at least a second one of a plurality of optical fibers toward second blazed Bragg gratings configured to generate acoustic energies for imaging second regions in response to the third optical signals;
sensing acoustic energies from the second regions and providing responsive fourth optical signals;
acquiring information from the responsive second and fourth optical signals;
generating an image of the first and second regions from the information;
tracking, using a laser tracking circuit of receive laser circuitry, a position of a point on a slope of a transmission notch generated within a reflection band by a pair of fiber Bragg gratings, wherein the first and second blazed Bragg gratings are positioned between the pair of fiber Bragg gratings; and
adjusting an operating characteristic of the pulsed transmit laser using a change in the position of the point to compensate for a change in temperature.

2. The method of claim 1, further comprising:
displaying the generated image on a display.

3. The method of claim 1, further comprising:
prior to generating the image, generating different polarization states using a polarization scrambler to mitigate an effect of at least one of optical birefringence and ultrasound induced birefringence.

4. The method of claim 1, wherein sensing acoustic energies from the first regions and providing responsive second optical signals includes:
transmitting, using a receive laser, a fifth optical signal on another one of the optical fibers, the fifth optical signal to be modulated by the acoustic energies to produce the second optical signals, the method further comprising:
prior to generating the image, obtaining first phase noise information from the receive laser during a first duration and second phase noise information from the receive laser during a second duration; and
subtracting the second phase noise information from the first phase noise information to improve a signal-to-noise ratio (SNR).

5. A method comprising:
tuning a pulsed transmit laser to a first wavelength and transmitting a first optical signal;
switching, using an optical switch circuit, the first optical signal from the pulsed transmit laser to an optical fiber toward a first blazed Bragg grating configured to generate acoustic energy for imaging a first region in response to the first optical signal;
sensing, using an interferometer including a first fiber Bragg grating (FBG) and a second FBG, acoustic energy from the region and providing a responsive second optical signal;
tuning the pulsed transmit laser to a second wavelength and transmitting a third optical signal,
switching, using the optical switch circuit, the third optical signals from the pulsed transmit laser to the optical fiber toward a second blazed Bragg grating configured to generate acoustic energy for imaging a second region in response to the third optical signal, wherein the first and second blazed Bragg gratings are positioned between the first and second FBGs;
sensing, using the interferometer, acoustic energy from the second region and providing a responsive fourth optical signal;
acquiring information from the responsive second and fourth optical signals;
generating an image of the first and second regions from the information;
tracking, using a laser tracking circuit of receive laser circuitry, a position of a point on a slope of a transmission notch generated within a reflection band by a pair of fiber Bragg gratings,
wherein the first and second blazed Bragg gratings are positioned between the pair of fiber Bragg gratings; and
adjusting an operating characteristic of the pulsed transmit laser using a change in the position of the point to compensate for a change in temperature.

6. The method of claim 5, further comprising:
displaying the generated image on a display.

7. The method of claim 5, further comprising:
prior to generating the image, generating different polarization states using a polarization scrambler to mitigate an effect of at least one of optical birefringence and ultrasound induced birefringence.

8. The method of claim 5, wherein sensing, using an interferometer including a first fiber Bragg grating (FBG) and a second FBG, acoustic energy from the region and providing a responsive second optical signal includes:
transmitting, using a receive laser, a fifth optical signal on another one of the optical fibers, the fifth optical signal to be modulated by the acoustic energy to produce the responsive second optical signal, the method further comprising:
prior to generating the image, obtaining first phase noise information during a first duration and second phase noise information during a second duration; and
subtracting the second phase noise information from the first phase noise information.

9. A system for generating images of a body lumen, the system comprising:
a pulsed transmit laser configured to transmit first optical signals at a first wavelength;
an optical switch circuit configured to switch the first optical signals from the pulsed transmit laser to at least a first one of a plurality of optical fibers toward first blazed Bragg gratings configured to generate acoustic energies for imaging a first region of the body lumen in response to the first optical signals;
receive laser circuitry including:
a receive laser configured to transmit second optical signals at a second wavelength on a second one of the plurality of optical fibers, the second optical signals to be modulated by the acoustic energies; and a laser tracking circuit configured to track a position of a point on a slope of a transmission notch generated within a reflection band by a pair of fiber Bragg gratings, wherein the first and second blazed Bragg gratings are positioned between the pair of fiber Bragg gratings:

data acquisition circuitry configured to acquire information from the modulated second optical signals; and a controller configured to:
- tune the transmit laser to the first wavelength;
- tune the receive laser to the second wavelength; and
- an imaging processing system configured to execute instructions that define an imaging algorithm to generate an image of the first region of the body lumen; and
- adjust an operating characteristic of the pulsed transmit laser using a change in the position of the point to compensate for a change in temperature.

* * * * *

UNITED STATES PATENT AND TRADEMARK OFFICE
CERTIFICATE OF CORRECTION

PATENT NO. : 10,327,645 B2
APPLICATION NO. : 15/026521
DATED : June 25, 2019
INVENTOR(S) : Rourke et al.

Page 1 of 1

It is certified that error appears in the above-identified patent and that said Letters Patent is hereby corrected as shown below:

On the Title Page

On page 4, in Column 2, under "Other Publications", Line 4, delete "Feb. 24, 2012]." and insert --May 24, 2012].-- therefor In the Specification In Column 12, Line 9, delete "550" and insert --545-- therefor In the Claims In Column 21, Line 17, in Claim 1, delete "signals," and insert --signals;-- therefor In Column 22, Line 8, in Claim 5, delete "signal," and insert --signal;-- therefor In Column 23, Line 6, in Claim 9, delete "gratings:" and insert --gratings;-- therefor Signed and Sealed this
Fourteenth Day of April, 2020

Andrei Iancu
*Director of the United States Patent and Trademark Office*